US012751923B2

(12) United States Patent
Ito et al.

(10) Patent No.: US 12,751,923 B2
(45) Date of Patent: Oct. 6, 2026

(54) NANOSTRUCTURE OR MICROSTRUCTURE AND METHOD FOR PRODUCING SAME

(71) Applicant: The University of Tokyo, Tokyo (JP)

(72) Inventors: Kohzo Ito, Tokyo (JP); Shuntaro Uenuma, Tokyo (JP); Yumi Shikano, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 330 days.

(21) Appl. No.: 18/290,051

(22) PCT Filed: May 9, 2022

(86) PCT No.: PCT/JP2022/019741
§ 371 (c)(1),
(2) Date: Nov. 9, 2023

(87) PCT Pub. No.: WO2022/239753
PCT Pub. Date: Nov. 17, 2022

(65) Prior Publication Data

US 2024/0299303 A1 Sep. 12, 2024

(30) Foreign Application Priority Data

May 10, 2021 (JP) ................................ 2021-079929

(51) Int. Cl.
*A61K 9/14* (2006.01)
*A23L 33/10* (2016.01)
(Continued)

(52) U.S. Cl.
CPC .............. *A61K 9/146* (2013.01); *A23L 33/10* (2016.08); *A61K 31/122* (2013.01); (Continued)

(58) Field of Classification Search
CPC ...................................................... A61K 9/146
See application file for complete search history.

(56) References Cited

U.S. PATENT DOCUMENTS 7,622,527 B2 * 11/2009 Ito .......................... C08G 83/00
525/54.44
2021/0338597 A1 11/2021 Ito et al.

FOREIGN PATENT DOCUMENTS

JP 2009-292727 12/2009
JP 2009-292727 A * 12/2009
(Continued)

OTHER PUBLICATIONS

Kobayashi et al, Precise synthesis of polyrotaxane and preparation of supramolecular materials based on its mobility, Polymer Journal, 53: 505-513. (Year: 2021).*
(Continued)

*Primary Examiner* — Carlos A Azpuru
(74) *Attorney, Agent, or Firm* — Wenderoth, Lind & Ponack, L.L.P.

(57) ABSTRACT

Provided is a nanostructure or a microstructure comprising a plurality of cyclic molecules, each of which is provided with an opening, and a plurality of chain-like molecules, the nanostructure or microstructure being such that each of the plurality of chain-like molecules is included in skewered fashion in some of the plurality of cyclic molecules, whereby a plurality of pseudo-polyrotaxanes and/or polyrotaxanes are formed, wherein some or all of the adjacent cyclic molecules in the nanostructure or microstructure crosslink with each other.

13 Claims, 7 Drawing Sheets

NANOSHEET

(51) Int. Cl.

| | |
|---|---|
| ***A61K 31/122*** | (2006.01) |
| ***A61K 31/352*** | (2006.01) |
| ***A61K 31/445*** | (2006.01) |
| ***A61K 31/513*** | (2006.01) |
| ***A61K 31/573*** | (2006.01) |

(52) U.S. Cl.

CPC .......... *A61K 31/352* (2013.01); *A61K 31/445* (2013.01); *A61K 31/513* (2013.01); *A61K 31/573* (2013.01)

(56) References Cited

FOREIGN PATENT DOCUMENTS

| | | |
|---|---|---|
| JP | 2012-155683 | 8/2012 |
| JP | 2012-156104 | 8/2012 |
| JP | 2019-041459 | 3/2019 |
| WO | 2020/013215 | 1/2020 |
| WO | 2020/175679 | 9/2020 |

OTHER PUBLICATIONS

International Search Report issued Jul. 26, 2022 in International (PCT) Application No. PCT/JP2022/019741.

* cited by examiner 10
20
20a
20b
20c 30
10
20

30
40
PSEUDO-POLYROTAXANE NANOSHEET
(PPR NANOSHEET)

50
CROSSLINKING
AGENT
10
50
42
CROSSLINKED PPR NANOSHEET
REMOVAL
OF AXIS
20

44
NANOSHEET

NANOSTRUCTURE OR MICROSTRUCTURE AND METHOD FOR PRODUCING SAME

TECHNICAL FIELD

The present invention relates to a nano- or micro-structural body including a plurality of pseudo-polyrotaxanes and/or polyrotaxanes, and a method of producing the structural body.

BACKGROUND ART

The inside of a cyclodextrin having a cyclic structure is hydrophobic, and hence the cyclodextrin incorporates a hydrophobic molecule (guest molecule) thereinto in water. In many cases, a strong hydrogen bond is formed between hydroxy groups in the cyclodextrin after the incorporation of the hydrophobic molecule, and hence the cyclodextrin spontaneously crystallizes. At this time, the cyclodextrin forms a single crystal of the order of micrometers. The shape and size (crystal habit) of the single crystal can be changed by controlling the kind and structure of a polymer serving as the guest molecule, and a crystal growth process.

The inventors have previously invented a nanosheet including a plurality of pseudo-polyrotaxanes and/or polyrotaxanes in each of which a linear molecule penetrates the cavity of a cyclic molecule in a skewered manner to be included in the cyclic molecule, and a method of producing the nanosheet (Patent Literatures 1 and 2). A synthesis process and a film formation process for such nanosheet are relatively simple, and the nanosheet is excellent in biosafety and compatibility. Accordingly, the nanosheet has been expected to find applications in various technical fields including a drug and a biomaterial.

CITATION LIST

Patent Literature

PTL 1: WO 2020/013215 A1

PTL 2: WO 2020/175679 A1

SUMMARY OF INVENTION

Technical Problem

Incidentally, in each of the isolated nanosheets described in Patent Literatures 1 and 2, the cyclic molecules arranged on the chain molecule in each pseudo-polyrotaxane and/or polyrotaxane can move along the chain molecule at a low inclusion ratio, and hence dilution with a specific solvent is liable to cause the degradation of the isolated nanosheet in some cases. In addition, in each of the isolated nanosheets described in Patent Literatures 1 and 2, the plurality of cyclic molecules are arranged under a state in which the respective cavities of the plurality of cyclic molecules are penetrated by the chain molecule in a skewered manner, and hence the chain molecule is present in the cavities of the cyclic molecules. Accordingly, the ratio of a space in each of the cavities of the cyclic molecules that may be utilized for the carrying of an external substance, such as the adsorption or inclusion of the substance, is low. It has been desired to solve at least one of those problems.

Solution to Problem

The present invention encompasses the following embodiments.

Item 1. A nano or microstructural body including: a plurality of cyclic molecules each including a cavity; and a plurality of chain molecules, the plurality of chain molecules each being included in part of the plurality of cyclic molecules in a skewered manner to form a plurality of pseudo-polyrotaxanes and/or polyrotaxanes, wherein all or part of the adjacent cyclic molecules in the nano or microstructural body are crosslinked to each other.

Item 2. The nano or microstructural body according to Item 1, wherein 50% or more of a total number of the cyclic molecules in the nano or microstructural body are crosslinked.

Item 3. The nano or microstructural body according to Item 1 or 2, wherein the plurality of cyclic molecules arranged in series in the nano or microstructural body form a column, and the number of the columns in which the chain molecules are free from being included accounts for more than 10% of a total number of the columns in the nano or microstructural body.

Item 4. The nano or microstructural body according to any one of Items 1 to 3, wherein the chain molecules in the plurality of pseudo-polyrotaxanes and/or polyrotaxanes each have, at both ends thereof or near both the ends, non-ionizable groups that are free from ionizing in water or an aqueous solution.

Item 5. The nano or microstructural body according to any one of Items 1 to 3, wherein the chain molecules in the plurality of pseudo-polyrotaxanes and/or polyrotaxanes each have, at both ends thereof or near both the ends, ionizable groups that ionize under conditions under which the nano or microstructural body is produced.

Item 6. The nano or microstructural body according to any one of Items 1 to 5, wherein the chain molecules each have, inside both ends of the chain molecule, a first region and a second region in which the cyclic molecules are absent, and the first region and the second region each have a length of from 0.5 nm to 100 nm.

Item 7. The nano or microstructural body according to any one of Items 1 to 6, wherein the cyclic molecules are selected from the group consisting of: α-cyclodextrin; β-cyclodextrin; γ-cyclodextrin; a crown ether; a pillararene; a calixarene; a cyclophane; a cucurbituril; and derivatives thereof.

Item 8. The nano or microstructural body according to any one of Items 1 to 7, wherein the cavity has included therein a substance.

Item 9. The nano or microstructural body according to any one of Items 1 to 8, wherein the microstructural body is a nanosheet.

Item 10. A substance adsorbent including the nano or microstructural body of any one of Items 1 to 9.

Item 11. A pharmaceutical including the nano or microstructural body of any one of Items 1 to 9.

Item 12. A pharmaceutical including the nano or microstructural body of any one of Items 1 to 9.

Item 13. A method of producing a nano or microstructural body including a step of crosslinking a nano or microstructural body, which includes a plurality of cyclic molecules each including a cavity and a plurality of chain molecules, and in which the plurality of chain molecules are each included in part of the plurality of cyclic molecules in a skewered manner to form a plurality of pseudo-polyrotaxanes and/or polyrotaxanes, to provide a nano or microstructural body in which all or part of the adjacent cyclic molecules are crosslinked to each other.

Item 14. The method according to Item 13, further including a step of removing part or all of the plurality of chain molecules included in part of the plurality of cyclic molecules in a skewered manner.

Advantageous Effects of Invention

According to the present invention, the cyclic molecules in the nano or microstructural body are more strongly bonded to each other, and hence the degradation of the nano or microstructural body hardly occurs.

BRIEF DESCRIPTION OF DRAWINGS

FIG. 3A is an illustration of the production example of a rod-shaped structural body in the case where its PEO is a short chain, FIG. 3B is an illustration of the production example of a cube-shaped structural body in the case where its PEO is longer than that of FIG. 3A, FIG. 3C is an illustration of the production example of a sheet-shaped structural body in the case where its PEO is even longer than that of FIG. 3B, and FIG. 3D is an illustration of the production example of a sheet-shaped structural body in the case where its PEO is even longer than that of FIG. 3C.

FIG. 5A is an illustration of a tripolymer having three segments in which a central portion is a PPO and both ends are each a PEO having a molecular weight of 0.2K, FIG. 5B is an illustration of a tripolymer having three segments in which a central portion is the PPO and both ends are each a PEO having a molecular weight of 1.1K, FIG. 5C is an illustration of a tripolymer having three segments in which a central portion is the PPO and both ends are each a PEO having a molecular weight of 6.5K, FIG. 5D is a schematic view (left) of a structural body formed by using the chain polymer of FIG. 5A, and an enlarged view (right) of a portion surrounded with a circle, FIG. 5E is a schematic view (left) of a structural body formed by using the chain polymer of FIG. 5B, and an enlarged view (right) of a portion surrounded with a circle, and FIG. 5F is a schematic view (left) of a structural body formed by using the chain polymer of FIG. 5C, and an enlarged view (right) of a portion surrounded with a circle.

DESCRIPTION OF EMBODIMENTS

Figures 1A, 1B, 1C, 1D, 1E:
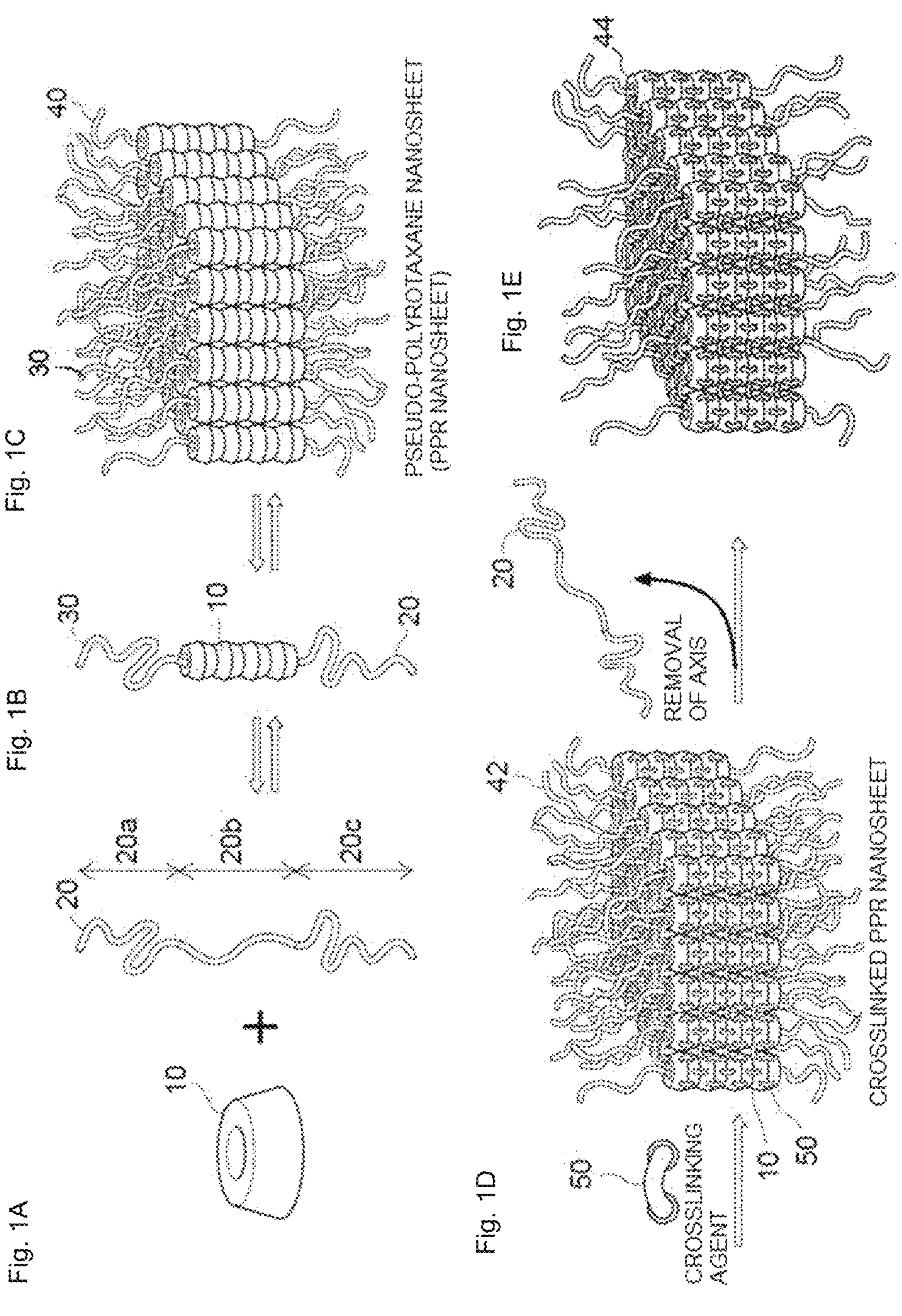
FIG. 1A, FIG. 1B, FIG. 1C, FIG. 1D, and FIG. 1E are each a schematic view for illustrating a method of producing a nanosheet of an embodiment of the present invention.

A mode for carrying out the present invention is described below.

According to an embodiment of the present invention, there is provided a nano or microstructural body including: a plurality of cyclic molecules each including a cavity; and a plurality of chain molecules, the plurality of chain molecules each being included in a corresponding part of the plurality of cyclic molecules in a skewered manner to form a plurality of pseudo-polyrotaxanes and/or polyrotaxanes, in which all or part of the adjacent cyclic molecules in the nano or microstructural body are crosslinked to each other.

The term "nano or microstructural body" as used herein refers to "a nanostructural body or a microstructural body." The term "nanostructural body" refers to the following structural body: the dimension of the crystal of the structural body along at least one of its a-axis, b-axis, or c-axis is 1 nm or more, and the dimension of the crystal of the structural body along each of the a-axis, the b-axis, and the c-axis is less than 1 μm. The term "microstructural body" refers to the following structural body: the dimension of the crystal of the structural body along at least one of its a-axis, b-axis, or c-axis is 1 μm or more.

The term "nanosheet" as used herein refers to a sheet-shaped nano or microstructural body in which the thickness of one layer of a nanosheet is less than 100 nm, preferably from 1 nm to 100 nm, more preferably from 3 nm to 50 nm, still more preferably from 5 nm to 20 nm. When the nanosheet is formed of a plurality of layers, the thickness of a single-layer nanosheet for forming the nanosheet is 100 nm or less, preferably from 1 nm to 100 nm, more preferably from 3 nm to 50 nm, still more preferably from 5 nm to 20 nm. When the dimension of the crystal of the structural body along each of its a-axis, b-axis, and c-axis is less than 1 μm, the nanosheet is a nanostructural body, and when the dimension of the crystal of the structural body along at least one of the a-axis, the b-axis, or the c-axis is 1 μm or more, the nanosheet is a microstructural body.

It is desired that the thickness direction of the nanosheet formed of a single layer be the lengthwise direction of each of the pseudo-polyrotaxanes and/or the polyrotaxanes, in other words, the lengthwise direction of each of the chain molecules. It is desired that the lengthwise direction of each of the pseudo-polyrotaxanes and/or the polyrotaxanes and the lengthwise direction of each of the chain molecules be the thickness direction of the isolated nanosheet formed of a single layer of the present application.

The nano or microstructural body of the embodiment of the present invention may be an isolated nano or microstructural body. In particular, the nanosheet may be an isolated nanosheet. The term "isolated" in the terms "isolated nano or microstructural body" and "isolated nanosheet" as used herein means that the nano or microstructural bodies, or the nanosheets can be present alone in a solution without assembling with each other. The "isolated nano or microstructural body" may be formed of a single layer, or may be formed of a plurality of layers. The "isolated nanosheet" may be formed of a single layer, or the nanosheet may be formed of a plurality of layers. The formation of the isolated nano or microstructural body may be recognized by small-angle X-ray scattering measurement, phase-contrast optical microscope observation, atomic force microscope observation, or scanning electron microscope observation. In particular, it can be recognized by small-angle X-ray scattering measurement through use of a shape factor that the isolated nanosheet has a sheet shape. Specifically, the formation of the isolated nanosheet can be recognized when the shape factor shows a fringe characteristic of a sheet structure, and no increase in scattering intensity due to aggregation is observed on a basic angle side (see, for example, "Principles and Applications of X-ray, Light and Neutron Scattering" (KS Chemical Specialized Book)).

The term "polyrotaxane" as used herein means a product having, at both the terminals of a chain molecule, groups (capping groups) each having an action (capping action) that prevents a cyclic molecule in which the chain molecule is included from desorbing from an inclusion state. Meanwhile, the term "pseudo-polyrotaxane" as used herein means a product that has a group (capping group) having the above-mentioned capping action only at one terminal of a chain molecule, or is free of groups (capping groups) each having the above-mentioned capping action at both the terminals of the chain molecule.

The phrase "the nano or microstructural body has a plurality of "pseudo-polyrotaxanes and/or polyrotaxanes"" as used herein means the case of having only the plurality of "pseudo-polyrotaxanes", the case of having only the plurality of "polyrotaxanes", or the case of having at least one kind of "pseudo-polyrotaxane" and at least one kind of "polyrotaxane", that is, having a plurality of the "pseudo-polyrotaxane(s)" and the "polyrotaxane(s)" in total.

Examples of the cyclic molecule may include, but not limited to, α-cyclodextrin ("cyclodextrin" is hereinafter sometimes simply referred to as "CD"), β-cyclodextrin, γ-cyclodextrin, a crown ether, a pillararene, a calixarene, a cyclophane, a cucurbituril, and derivatives thereof. In terms of easy production of a sheet, applications thereof, and the like, α-cyclodextrin, β-cyclodextrin, and γ-cyclodextrin are preferred. Examples of the derivatives may include, but not limited to, methylated α-cyclodextrin, methylated β-cyclodextrin, methylated γ-cyclodextrin, hydroxypropylated α-cyclodextrin, hydroxypropylated β-cyclodextrin, and hydroxypropylated γ-cyclodextrin. One nano or microstructural body may include one or two or more kinds of cyclic molecules.

The chain molecules for forming the pseudo-polyrotaxanes and/or the polyrotaxanes for forming the nano or microstructural body each preferably have, inside both of its ends, first and second regions in which the cyclic molecules are absent (hereinafter sometimes simply referred to as "cyclic molecule-free regions"). That is, the first region is present inside one end of a first chain molecule, and the second region is present inside the other end of the first chain molecule.

The lengths of the first and second regions are each independently desirably from 0.5 nm to 100 nm, preferably from 1 nm to 70 nm, more preferably from 1 nm to 50 nm. The presence of the "cyclic molecule-free regions" each having the above-mentioned length may advantageously act on the formation of, in particular, an isolated nanosheet, though this assumption is not based on a perfect theory. The thickness of the nanosheet and the lengths of the chain molecules may be determined by small-angle X-ray scattering or with an atomic force microscope.

Each of the chain molecules may be linear, that is, a single chain, or may be a branched chain. Preferred examples of the branched chain include a trifurcated chain (having one branching point) and a quadrifurcated chain (having two branching points).

The chain molecules may each be a polymer having a repeating structure of the same monomer in its entirety, a block copolymer including at least two blocks, or a block copolymer including at least three blocks.

Each block of the "block copolymer" is preferably formed only of one repeating unit, but may have a first spacer group between one repeating unit and the next repeating unit.

In addition, the "block copolymer" may have, between adjacent blocks thereof, a second spacer group, which may be identical to or different from the first spacer group.

Examples of the first spacer group and/or the second spacer group may include, but not limited to: a linear or branched alkylene group having 1 to 20 carbon atoms, such as a methylene group, an ethylene group, a propylene group, a butylene group, or a pentylene group (part of which may be substituted with an aromatic ring such as a phenyl group); ethers of linear or branched chains each having 1 to 20 carbon atoms; esters of linear or branched chains each having 1 to 20 carbon atoms; and an aromatic group having 6 to 24 carbon atoms such as a phenyl group.

The cyclic molecules may each have included therein one block out of at least two blocks of a chain molecule including the at least two blocks, or one block (in particular, a central block) out of at least three blocks.

In the present application, as described above, the chain molecules are not particularly limited as long as the chain molecules can assume a form in which the chain molecules are included in the cyclic molecules in a skewered manner.

Examples of the skeleton of the chain molecule include: a long chain fatty acid having 12 or more carbon atoms; and a polymer selected from the group consisting of: polyvinyl alcohol; polyvinylpyrrolidone; poly(meth)acrylic acid; a cellulose-based resin (e.g., carboxymethylcellulose, hydroxyethylcellulose, or hydroxypropylcellulose); polyacrylamide; polyethylene oxide; polyethylene glycol; polypropylene glycol; a polyvinyl acetal-based resin; polyvinyl methyl ether; polyamine; polyethyleneimine; casein; gelatin; starch; and/or copolymers thereof; a polyolefin-based resin, such as polyethylene, polypropylene, or a copolymer resin with any other olefin-based monomer; a polyester resin; a polyvinyl chloride resin; a polystyrene-based resin, such as polystyrene or an acrylonitrile-styrene copolymer resin; an acrylic resin, such as polymethyl methacrylate, a (meth)acrylic acid ester copolymer, or an acrylonitrile-methyl acrylate copolymer resin; a polycarbonate resin; a polyurethane resin; a vinyl chloride-vinyl acetate copolymer resin; a polyvinyl butyral resin; and derivatives or modified products thereof; polyisobutylene; polytetrahydrofuran; polyaniline; an acrylonitrile-butadiene-styrene copolymer (ABS resin); polyamides such as nylon; polyimides; polydienes, such as polyisoprene and polybutadiene; polysiloxanes such as polydimethylsiloxane; polysulfones; polyimines; polyacetic anhydrides; polyureas; polysulfides; polyphosphazenes; polyketones; polyphenylenes; polyhaloolefins; and derivatives thereof. For example, the polymer is desirably selected from the group consisting of: polyethylene glycol; polyisoprene; polyisobutylene; polybutadiene; polypropylene glycol; polytetrahydrofuran; polydimethylsiloxane; polyethylene; polypropylene; polyvinyl alcohol; and polyvinyl methyl ether. In particular, the polymer is desirably polyethylene glycol or polypropylene glycol. Two or more different kinds selected from those polymers may form at least two or at least three blocks.

When the chain molecules each have, for example, at least two or at least three blocks, it is desired that the weight average molecular weight of the chain molecules themselves be from 500 to 500,000, preferably from 1,000 to 20,000, more preferably from 6,000 to 16,000. The weight average molecular weight of the chain molecules may be measured by gel permeation chromatography (GPC). Although measurement conditions for GPC depend on the kinds of the chain molecules, it is desired that the kinds of eluent and column, a temperature, a standard substance, and a flow rate be appropriately selected.

The chain molecules are each preferably a water-soluble chain molecule. The water-soluble chain molecule is not particularly limited as long as the molecule has water solubility, for example, a characteristic that allows 1 g thereof to be dissolved in 1 L of water.

Examples of the skeleton, for example, the skeleton forming at least two or at least three blocks of the water-soluble chain molecule may include, but not limited to, polyethylene glycol, polypropylene glycol, polyvinyl alcohol, polyethyleneimine, polyacrylic acid, polymethacrylic acid, polyacrylamide, pullulan, water-soluble cellulose derivatives such as hydroxypropylcellulose, polyvinylpyrrolidone, polypeptide, and copolymers each including polyethylene glycol.

That is, it is desired that the water-soluble chain molecule be at least one kind selected from the group consisting of the polymers listed above, preferably at least one kind selected from the group consisting of: polyethylene glycol; polypropylene glycol; polyvinyl alcohol; polyethyleneimine; and copolymers including polyethylene glycol, more preferably at least one kind selected from the group consisting of: polyethylene glycol; and polypropylene glycol. For example, when the chain molecules are each a water-soluble chain molecule formed of one kind of polymer, the polymer may be formed of only polyethylene glycol, only polypropylene glycol, only polyvinyl alcohol, only polyethyleneimine, or only polyethylene glycol. When the chain molecules are each a water-soluble chain molecule formed of three blocks, the central block may be polypropylene glycol, and the blocks on each side thereof may be polyethylene glycol.

The molecular weight of the water-soluble chain molecule (number average molecular weight or weight average molecular weight) is not particularly limited, but it is desired that the molecular weight be from 500 to 500,000, preferably from 1,000 to 50,000, more preferably from 2,000 to 20,000.

The plurality of chain molecules of the pseudo-polyrotaxanes and/or the polyrotaxanes for forming the nano or microstructural body may be one kind of chain molecule, or may be two or more kinds of chain molecules. However, the chain molecules are preferably formed essentially of one kind of chain molecule, and are more preferably formed only of one kind of chain molecule. The phrase "formed essentially of one kind of chain molecule" means that another kind of "chain molecule" is also present as a chain molecule of the pseudo-polyrotaxanes and/or the polyrotaxanes for forming the nano or microstructural body, but is present to such an extent that the presence does not adversely affect the formation of the nano or microstructural body. In addition, the phrase "formed only of one kind of chain molecule" means that no chain molecule other than the kind of chain molecule is present as a chain molecule of the pseudo-polyrotaxanes and/or the polyrotaxanes for forming the nano or microstructural body.

An inclusion ratio is the ratio of the cyclic molecules in the pseudo-polyrotaxanes and/or the polyrotaxanes, and is the ratio of the amount of the chain molecules included in the cyclic molecules to the maximum amount of the chain molecules included in the cyclic molecules (when a specified inclusion ratio is 100%).

For example, when the chain molecules are each polyethylene glycol (PEG), and the cyclic molecules are each α-cyclodextrin, it has been known that the thickness of two repeating units of the polyethylene glycol is equal to the thickness of α-cyclodextrin. Accordingly, a specified inclusion ratio when a ratio between the number of moles of α-cyclodextrin and the number of the repeating units of the polyethylene glycol is set to 1:2 is defined as 100%.

The inclusion ratio may be determined by small-angle X-ray scattering (SAXS) measurement of an obtained nano or microstructural body dispersion. Specifically, the inclusion ratio may be determined from the ratio between: the thickness of the sheet determined by fitting a one-dimensional SAXS profile of a dispersion of pseudo-polyrotaxanes and/or polyrotaxanes through use of a formula assuming a sheet-like structure; and the fully stretched trans chain length of the chain molecule.

In the present application, the inclusion ratio of the pseudo-polyrotaxanes and/or the polyrotaxanes is from 1% to 100%, preferably from 5% to 100%, more preferably from 10% to 100%, most preferably from 20% to 100%.

After the formation of the nano or microstructural body including the plurality of pseudo-polyrotaxanes and/or polyrotaxanes as described in each of, for example, WO 2020/013215 A1 and WO 2020/175679 A1, when the adjacent cyclic molecules are crosslinked by a known method of crosslinking cyclic molecules such as the use of a crosslinking agent, a nano or microstructural body in which the adjacent cyclic molecules are crosslinked to each other can be obtained. Details about the crosslinking of the cyclic molecules are described later in relation to a method of producing a nano or microstructural body of an embodiment of the present invention.

In the case of, for example, a nano or microstructural body in which its chain molecules are each a polyethylene oxide-polypropylene oxide-polyethylene oxide (PEO-PPO-PEO) triblock polymer, and its cyclic molecules are each a cyclodextrin, the nano or microstructural body before its crosslinking reaction is dissolved when diluted with water, but after the crosslinking reaction, the nano or microstructural body is not dissolved even when diluted with water. As described above, the crosslinking improves the stability of the nano or microstructural body against a solvent. Further, the crosslinking of the cyclic molecules makes a structural body in the nano or microstructural body stronger, and hence a function of carrying a target molecule on a pore of the nano or microstructural body (a space in a column defined and formed by the plurality of cyclic molecules, a cavity defined and formed by one cyclic molecule, or a space between the plurality of pseudo-polyrotaxanes and/or polyrotaxanes), the surface adhesion property of the target molecule (substance to be adsorbed) derived from the structure of the nano or microstructural body, and the like can be improved.

Although the ratio of the crosslinked cyclic molecules out of the total number of the cyclic molecules in the nano or microstructural body is not particularly limited, the ratio is 10% or more, 20% or more, 30% or more, 40% or more, 50% or more, 60% or more, 70% or more, 80% or more, 90% or more, or 100%. As the ratio at which the cyclic molecules are crosslinked becomes higher, an effect, such as the suppression of the degradation of the nano or microstructural body resulting from the stability of the structure of the nano or microstructural body, or a function of carrying a target molecule or the surface adhesion property effect of the molecule, is improved.

The crosslinking of the cyclic molecules in the nano or microstructural body includes: adjacent crosslinking in one molecule of the plurality of pseudo-polyrotaxanes and/or polyrotaxanes, in other words, the serial crosslinking of the adjacent cyclic molecules along the lengthwise direction of the chain molecule of one molecule of the plurality of pseudo-polyrotaxanes and/or polyrotaxanes; and the crosslinking of the cyclic molecules in adjacent molecules of the pseudo-polyrotaxanes and/or the polyrotaxanes, in other words, parallel crosslinking.

The serial crosslinking of the adjacent cyclic molecules means that the adjacent cyclic molecules out of the plurality of cyclic molecules in each of some or all pseudo-polyrotaxanes and/or polyrotaxanes out of the plurality of pseudo-polyrotaxanes and/or polyrotaxanes are crosslinked to each other.

The parallel crosslinking of the cyclic molecules in adjacent molecules of the pseudo-polyrotaxanes and/or the polyrotaxanes means that the cyclic molecules in some or all adjacent pseudo-polyrotaxanes and/or polyrotaxanes out of the plurality of pseudo-polyrotaxanes and/or polyrotaxanes are crosslinked to each other.

In some embodiments, the crosslinking of the cyclic molecules in the nano or microstructural body includes the serial crosslinking of the adjacent cyclic molecules in the adjacent crosslinking in one molecule of the plurality of pseudo-polyrotaxanes and/or polyrotaxanes. In some other embodiments, the crosslinking of the cyclic molecules in the nano or microstructural body includes the parallel crosslinking of the cyclic molecules in adjacent molecules of the pseudo-polyrotaxanes and/or the polyrotaxanes. In some preferred embodiments, the crosslinking of the cyclic molecules in the nano or microstructural body includes both of: the serial crosslinking of the adjacent cyclic molecules in the adjacent crosslinking in one molecule of the plurality of pseudo-polyrotaxanes and/or polyrotaxanes; and the parallel crosslinking of the cyclic molecules in the adjacent molecules of the pseudo-polyrotaxanes and/or the polyrotaxanes. When the cyclic molecules are crosslinked by both of the above-mentioned crosslinkings, the structure of each of the cyclic molecules in the nano or microstructural body becomes stronger.

Although the nano or microstructural body may be formed only from the molecules of the plurality of pseudo-polyrotaxanes and/or polyrotaxanes, a column-only portion including a plurality of cyclic molecules in which no chain molecule is present in the cyclic molecules may be present. As described later, the nano or microstructural body including the column-only portion including the plurality of cyclic molecules may be produced by removing the chain molecules from part or all of the molecules of the plurality of pseudo-polyrotaxanes and/or polyrotaxanes in the nano or microstructural body whose cyclic molecules are crosslinked.

In some preferred embodiments, the plurality of cyclic molecules arranged in series in the nano or microstructural body form a column, and the number of the columns in which the chain molecules are not included accounts for more than 10%, more preferably 20% or more, still more preferably 30% or more, still more preferably 40% or more, still more preferably 50% or more of the total number of the columns in the nano or microstructural body. In a preferred specific embodiment, the plurality of cyclic molecules arranged in series in the nano or microstructural body form a column, and the number of the columns in which the chain molecules are not included accounts for 100% of the total number of the columns in the nano or microstructural body. In such nano or microstructural body, a function of carrying a target molecule, the surface adhesion property of the target molecule, and the like can be further improved.

In some preferred embodiments, the number of the columns in which the chain molecules are included accounts for less than 90%, more preferably 80% or less, still more preferably 70% or less, still more preferably 60% or less, still more preferably 50% or less of the total number of the columns in the nano or microstructural body.

In some embodiments, the chain molecules in the plurality of pseudo-polyrotaxanes and/or polyrotaxanes of the nano or microstructural body each have, at both of its ends or near both the ends, non-ionizable groups that do not ionize in water or an aqueous solution.

The phrase "near the chain molecules" typically refers to the range of 1 to 10 monomer units, more preferably 1 to 5 monomer units from a terminal of each of the chain molecules excluding the terminal of the chain molecule.

The term "non-ionizable group" as used herein refers to a group that does not ionize in water or an aqueous solution.

The non-ionizable group is not particularly limited as long as the above-mentioned definitions are satisfied. However, the non-ionizable group is desirably, for example, at least one kind selected from the group consisting of: an isopropyl group; a sec-butyl group; a tert-butyl group; a neopentyl group; an isopentyl group; a sec-pentyl group; a 3-pentyl group; a tert-pentyl group; a cyclopentyl group; a pentene group; a hexyl group; a hexene group; a heptyl group; a heptene group; an octyl group; an octene group; a nonyl group; a nonene group; a decyl group; a decene group; an undecyl group; an undecene group; a dodecyl group; a dodecene group; a tridecyl group; a tridecene group; a tetradecyl group; a tetradecene group; a pentadecyl group; a pentadecene group; a hexadecyl group; a hexadecene group; a heptadecyl group; a heptadecene group; an octadecyl group; an octadecene group; a nonadecyl group; a nonadecene group; an eicosyl group; an eicosene group; a heneicosyl group; a heneicosene group; a tetracosyl group; a tetracosene group; a triacontyl group; a triacontene group; and isomers thereof; a 4-isopropylbenzenesulfonyl group; a 1-octanesulfonyl group; a 4-biphenylsulfonyl group; a 4-tert-butylbenzenesulfonyl group; a 2-mesitylenesulfonyl group; a methanesulfonyl group; a 2-nitrobenzenesulfonyl group; a 4-nitrobenzenesulfonyl group; a pentafluorobenzenesulfonyl group; a 2,4,6-triisopropylbenzenesulfonyl group; a p-toluenesulfonyl group; a non-ionizing hydroxy group; a heptafluorobutyroyl group; a pivaloyl group; a perfluorobenzoyl group; a non-ionizing amino group ($-NH_2$); a non-ionizing carboxylic acid group ($-COOH$); and an isovaleryl group. In addition, the non-ionizable group is preferably at least one kind selected from the group consisting of: a non-ionizing hydroxy group; a heptafluorobutyroyl group; a perfluorobenzoyl group; and an isovaleryl group, more preferably at least one kind selected from the group consisting of: a perfluorobenzoyl group; and an isovaleryl group.

As described above, the term "non-ionizing" in each of the terms "non-ionizing hydroxy group," "non-ionizing amino group," and "non-ionizing carboxylic acid group" means that such group is not ionizing in water or an aqueous solution.

When the non-ionizable groups are present at both the ends of each of the chain molecules or near both the ends, one of the non-ionizable groups may be identical to or different from the other non-ionizable group. Each of the non-ionizable groups may be directly bonded to a block of the chain molecules, or may be indirectly bonded thereto through a spacer.

The following nano or microstructural body is advantageous in that the adhesion or aggregation of the nano or microstructural bodies is suppressed: the chain molecules in the plurality of pseudo-polyrotaxanes and/or polyrotaxanes of the nano or microstructural body each include, at both of its ends or near both the ends, the non-ionizable groups that do not ionize in water or an aqueous solution.

In some preferred embodiments, the chain molecules in the plurality of pseudo-polyrotaxanes and/or polyrotaxanes of the nano or microstructural body each have, at both of its ends or near both the ends, ionizable groups that ionize under the conditions under which the nano or microstructural body is produced.

The phrase "near the chain molecules" typically refers to the range of 1 to 10 monomer units, more preferably 1 to 5 monomer units from a terminal of each of the chain molecules excluding the terminal of the chain molecule.

The ionizable group is not particularly limited, but is desirably, for example, at least one kind selected from the group consisting of: a carboxyl group; an amino group; a sulfo group; a phosphoric acid group; a trimethylamino chloride group; a triethylamino chloride group; a dimethylamino group; a diethylamino group; a methylamino group; an ethylamino group; a pyrrolidine group; a pyrrole group; an ethyleneimine group; a piperidine group; a pyridine group; a pyrylium ion group; a thiopyrylium ion group; a hexamethyleneimine group; an azatropyrylene group; an imidazole group; a pyrazole group; an oxazole group; a thiazole group; an imidazoline group; a morpholine group; a thiazine group; a triazole group; a tetrazole group; a pyridazine group; a pyrimidine group; a pyrazine group; an indole group; a benzimidazole group; a purine group; a benzotriazole group; a quinoline group; a quinazoline group; a quinoxaline group; a pteridine group; a carbazole group; a porphyrin group; a chlorin group; a choline group; an adenine group; a guanine group; a cytosine group; a thymine group; a uracil group; a dissociated thiol group; a dissociated hydroxy group; an azido group; a pyridine group; carbamic acids, guanidines; sulfenic acids; ureas; thioureas; peroxy acids; and analogs and derivatives thereof.

When the ionizable groups are present at both the ends of each of the chain molecules or near both the ends, one of the ionizable groups may be identical to or different from the other ionizable group. Each of the above-mentioned ionizable groups may be directly bonded to the block of the chain molecules, or may be indirectly bonded thereto through a spacer.

The following nano or microstructural body is advantageous in that the adhesion or aggregation of the nano or microstructural bodies is suppressed: the chain molecules in the plurality of pseudo-polyrotaxanes and/or polyrotaxanes of the nano or microstructural body each include, at both of its ends or near both the ends, the ionizable groups that ionize in water or an aqueous solution.

The nano or microstructural body of the embodiment of the present invention, which includes the plurality of pseudo-polyrotaxanes and/or polyrotaxanes, may include a component except the above-mentioned "pseudo-polyrotaxanes and/or polyrotaxanes" as long as a configuration as the nano or microstructural body can be maintained.

Examples of such component may include, but not limited to: a first substance that can be included in the cavities of the above-mentioned cyclic molecules (also referred to as "first cyclic molecules") for forming the pseudo-polyrotaxanes and/or polyrotaxanes; second cyclic molecules that may be identical to or different from the first cyclic molecules; a second substance that can be included in the cavities of the second cyclic molecules; a third substance, which is different from the second substance and cannot be brought into the state of being included in the first and second cyclic molecules; and a pseudo-polyrotaxane and/or a polyrotaxane except the "specific" pseudo-polyrotaxanes and/or polyrotaxanes of the present invention.

Examples of the second cyclic molecules may include, but not limited to, the molecules listed as the first cyclic molecules.

Examples of the first and second substances include, but not limited to, a drug, a fluorescent substance, and a chromogenic enzyme.

Examples of the drug include, but not limited to, any drugs, including donepezil, 5-fluorouracil, hydrocortisone, betamethasone, menadione, and pharmaceutically acceptable salts thereof.

Examples of the fluorescent substance include, but not limited to, rhodamine, Nite red, poly-L-lysine-fluorescein isothiocyanate (FITC), coumarin, Cy2, Cy3, and Cy5.

Examples of the chromogenic enzyme include, but not limited to, horseradish peroxidase (HRP), alkaline phosphatase, β-galactosidase, glucose oxidase, and luciferase. The second substance may be identical to or different from the first substance.

The third substance may be selected depending on fields in each of which the isolated nano or microstructural body of the present invention is used or applied. Examples thereof may include, but not limited to: polymer materials that do not form inclusion complexes with cyclic molecules, such as polystyrene, polyvinylpyridine, polypyridine, polyphenylene, polyacrylamide, polyacrylic acid, polymethacrylic acid, polyvinyl alcohol, polyamide, polyester, polyimide, polybenzoxazole, polyvinyl chloride, polypropylene, polysilane, and polysiloxanes; biopolymers and biomolecules, such as DNA, protein, and polypeptide; inorganic nanomaterials, such as silica nanoparticles, titanium oxide nanoparticles, and silicon nanoparticles; carbon materials, such as fullerene, carbon nanotubes, graphene, graphite, and carbon quantum dots; and metal nanomaterials, such as gold nanoparticles, perovskite quantum dots, CdSeS/ZnS quantum dots, and iron oxide nanoparticles.

The first substance may be housed in a cavity defined and formed by the one first cyclic molecule, or may be housed in a space defined and formed by the plurality of first cyclic molecules arranged in series.

The second substance may be housed in a cavity defined and formed by the one second cyclic molecule, or may be housed in a space defined and formed by the plurality of second cyclic molecules arranged in series.

The third substance is bonded to the chain molecule, is bonded to the first or second cyclic molecule, or is held in a space between the plurality of pseudo-polyrotaxanes and/or polyrotaxanes (i.e., when a plurality of, in particular, 2, 3, or 4 columns serving as columnar structures formed of the pseudo-polyrotaxanes and/or polyrotaxanes are present, a space therebetween). When the third substance is bonded to the chain molecule, the substance is preferably bonded to each of both the ends, or one end, of the chain molecule, or the vicinity of the end, but may be bonded to another site of the chain molecule.

The size of the space between the plurality of pseudo-polyrotaxanes and/or polyrotaxanes, the size of the cavity defined and formed by the one first cyclic molecule, and the size of the space defined and formed by the plurality of first cyclic molecules arranged in series may be appropriately changed by changing, for example, the length of each of the chain molecules, the hydrophilicity and hydrophobicity of the chain molecule, and the kinds of the first cyclic molecules. Accordingly, the size of the cavity defined and formed by the cyclic molecule and/or the size of the space defined and formed by the cyclic molecules only needs to be appropriately changed in accordance with the size of the substance that is wished to be housed in such cavity or space.

The nano or microstructural body of the embodiment of the present invention can be formed from molecules each of which is highly safe for a living body and has high biocompatibility, such as cyclodextrin and polyethylene glycol, and hence is suited for utilization in a living body.

The nano or microstructural body of the embodiment of the present invention may be used for, for example, a material for drug delivery (e.g., a vehicle for drug delivery), a vehicle for carrying a food ingredient (except a pharmaceutical), bioimaging, a surface modifier, an adhesive, an adsorbent for a target substance, a wound site adhesion-preventing agent, a hair care material, a coating material, an oral care material such as a mouse wash, a supplement base, an aggregation control material for cells, algae, and the like, an oxygen barrier material, a moisturizing agent, a UV protection material, an odor-preventing material, and the like, but is not limited thereto.

According to an embodiment of the present invention, there is provided a material including the above-mentioned nano or microstructural body. Such material depends on fields in each of which the isolated nano or microstructural body of the present invention is used or applied, and examples thereof may include, but not limited to, a structural material, an artificial prosthetic material, a packaging material, a rubber material, a hair care material, a coating material, a paint, an oral care material such as a mouse wash, an adhesive, a supplement base, a high performance beverage, an aggregation control material, an oxygen barrier material, a moisturizing agent, a UV protection material, and an odor-preventing material.

According to embodiments of the present invention, there are provided a food, a pharmaceutical, and a cosmetic each including the above-mentioned nano or microstructural body. A food component in the food, a drug in the pharmaceutical, and a component in the cosmetic may each be carried by or included in the nano or microstructural body. The term "food" as used herein is a concept encompassing a wide variety of products that can be orally taken, and a beverage is included therein. The food encompasses an enteral food, a food for special dietary uses, foods with health claims including a food for specified health uses, a food with nutrient function claims, and a food with functional claims in addition to general foods including a health food. The health food encompasses a food provided in the name of, for example, a nutritional supplement, a health supplement, or a supplement. The "food", the "pharmaceutical", and the "cosmetic" may also be referred to as "food composition," "pharmaceutical composition," and "cosmetic composition," respectively.

According to an embodiment of the present invention, there is provided a method of producing a nano or microstructural body including a step of crosslinking a nano or microstructural body, which includes a plurality of cyclic molecules each including a cavity and a plurality of chain molecules, and in which the plurality of chain molecules are each included in part of the plurality of cyclic molecules in a skewered manner to form a plurality of pseudo-polyrotaxanes and/or polyrotaxanes, to provide a nano or microstructural body in which all or part of the adjacent cyclic molecules in the nano or microstructural body are crosslinked to each other.

Reference is made to FIG. 1A to FIG. 1E not for limiting the present invention but for promoting the understanding thereof. In FIG. 1A, a cyclic molecule 10 and a chain polymer 20 serving as a chain molecule are prepared, and are mixed in water or an aqueous solution. Examples of the aqueous solution may include, but not limited to, an aqueous solution of an alcohol, an aqueous solution of an acid, an aqueous solution of an alkali, a buffer, a culture medium, and blood plasma. For example, the cyclic molecule 10 may be a cyclodextrin, the chain polymer 20 is a chain polymer formed of three blocks 20*a*, 20*b*, and 20*c*, the blocks 20*a* and 20*c* are each polyethylene glycol, and the block 20*b* is polypropylene glycol. When the cyclic molecule 10 and the chain polymer 20 are mixed, as illustrated in FIG. 1B, the chain polymer 20 penetrates the plurality of cyclic molecules 10 in a skewered manner to produce a pseudo-polyrotaxane 30 in which the block 20*b* of the chain polymer 20 is included in the plurality of cyclic molecules 10. The aggregation of the plurality of pseudo-polyrotaxanes can provide a nanosheet 40 serving as a nano or microstructural body including the plurality of pseudo-polyrotaxanes 30 as illustrated in FIG. 1C.

The method of producing a nanosheet of the embodiment of the present invention may optionally include a step of introducing the above-mentioned non-ionizable groups in advance, or introducing the ionizable groups, into both the ends of each of the chain molecules or the vicinities thereof before the mixing with the cyclic molecules.

Further, the method of producing a nanosheet of the embodiment of the present invention may include a step of modifying the pseudo-polyrotaxanes before the obtainment of the nanosheet or part of the pseudo-polyrotaxanes of the resultant nanosheet.

The modifying step may be a step of introducing a substituent into an end of each of the chain molecules. As long as the isolated nanosheet is obtained, the substituent may be a capping group having such a capping action as to prevent dissociation of the cyclic molecules, may be a group having the action of a non-ionizable group and/or an ionizable group, or may be a group having any other action. The first substituent may have any combination of those actions, and may exhibit all the actions.

Examples of the group having a capping action and having the action of a non-ionizable group may include, but not limited to, an adamantane group, a neopentyl group, an isopentyl group, a sec-pentyl group, a 3-pentyl group, a tert-pentyl group, a cyclopentyl group, a pentene group, a hexyl group, a hexene group, a heptyl group, a heptene group, an octyl group, an octene group, a nonyl group, a nonene group, a decyl group, a decene group, an undecyl group, an undecene group, a dodecyl group, a dodecene group, a tridecyl group, a tridecene group, a tetradecyl group, a tetradecene group, a pentadecyl group, a pentadecene group, a hexadecyl group, a hexadecene group, a heptadecyl group, a heptadecene group, an octadecyl group, an octadecene group, a nonadecyl group, a nonadecene group, an eicosyl group, an eicosene group, a heneicosyl group, a heneicosene group, a tetracosyl group, a tetracosene group, a triacontyl group, a triacontene group, and isomers thereof.

For example, a group derived from folic acid, biotin, fluorescein, an oligopeptide, such as RGD or GRGDS, or a monoclonal antibody, such as rituximab, bevacizumab, tocilizumab, or infliximab, may be introduced as the group having the action of an ionizable group. For example, when a group derived from folic acid is to be introduced, the introduction may be performed by subjecting the isolated sheet to be obtained and folic acid to a reaction in the presence of a condensing agent, such as 4-(4,6-dimethoxy-1,3,5-triazin-2-yl)-4-methylmorpholinium chloride (DMT/MM), N,N'-dicyclohexylcarbodiimide (DCC), 1-(3-dimethylaminopropyl)-3-ethylcarbodiimide (EDC), benzotriazol-1-yloxy-trisdimethylaminophosphonium salt (BOP), (benzotriazol-1-yloxy)tripyrrolizidinophosphonium hexafluorophosphate (PyBOP), or O-(7-azabenzotriazol-1-yl)-N,N,N',N'-tetramethyluronium hexafluorophosphate (HATU).

As described in each of, for example, WO 2020/013215 A1 and WO 2020/175679 A1, the above-mentioned method of producing a nanosheet, which includes a plurality of cyclic molecules each including a cavity and a plurality of chain molecules, and in which the plurality of chain molecules are each included in a corresponding part of the plurality of cyclic molecules in a skewered manner to form a plurality of pseudo-polyrotaxanes and/or polyrotaxanes, is known.

In the method of producing a nanosheet of the embodiment of the invention of the present application, further, as illustrated in FIG. 1D, the nanosheet 40 is crosslinked with a crosslinking agent 50 or the like to provide a nanosheet 42 in which the adjacent cyclic molecules out of the plurality of cyclic molecules in each of some or all pseudo-polyrotaxanes and/or polyrotaxanes out of the plurality of pseudo-polyrotaxanes and/or polyrotaxanes are crosslinked to each other.

The crosslinking between the adjacent cyclic molecules is known, and see, for example, E. Renard et al., European Polymer Journal, Volume 33, Issue 1, Pages 49-57, 1997; Harada et al., Nature volume 364, pages 516-518, 1993; Furukawa et al., Angewandte Chemie Volume 51, Issue 42, Pages 10566-10569, 2012; and Zhu et al., Langmuir 2013, 29, 20, 5939-5943, 2013.

In a method of crosslinking the adjacent cyclic molecules through a crosslinking agent having a reactive functional group that can react with each of the functional groups of the cyclic molecules, the combination of the functional groups of the cyclic molecules and the crosslinking agent having a reactive functional group that can react with each of the functional groups of the cyclic molecules is known. Examples of the functional group of the cyclic molecule include a hydroxy group, a carboxyl group, and an amino group. Examples of the reactive functional group of the crosslinking agent include an isocyanate group, a thioisocyanate group, an epoxy group, and a dicarboxylic anhydride group. The crosslinking agent having two or more reactive functional groups is advantageous in that two cyclic molecules can be crosslinked via one molecule of the crosslinking agent. Examples of such compound having two or more reactive functional groups may include, but not limited to, an oxirane compound, such as epichlorohydrin or epibromohydrin, a diisocyanate such as hexamethylene diisocyanate, an oxetane compound such as 3-(chloromethyl)-3-methyloxetane, a tricarboxylic acid chloride such as 1,3,5-benzenetricarbonyl trichloride, and a dicarboxylic acid chloride, such as adipic acid dichloride, glutaric acid dichloride, 4,4'-oxydibenzoyl chloride, oxalic acid dichloride, succinic acid dichloride, suberic acid dichloride, terephthaloyl dichloride, diglycolyl chloride, 2,5-furandicarbonyl dichloride, or sebacic acid dichloride.

For example, in E. Renard et al., European Polymer Journal, Volume 33, Issue 1, Pages 49-57, 1997, there is a description of the crosslinking of a hydroxy group of β-cyclodextrin through use of epichlorohydrin as a crosslinking agent, as shown in the following scheme 1.

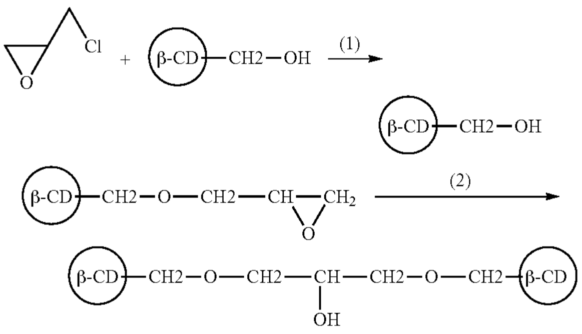

The crosslinking reaction may be performed in an aqueous solution or an organic solvent. Preferred examples of the solvent include, but not limited to, water, acetone, ethanol, ethyl methyl ketone, glycerin, ethyl acetate, methyl acetate, diethyl ether, cyclohexane, dichloromethane, 1,1,2-tetrafluoroethane, 1,1,2-trichloroethene, 1-butanol, 2-butanol, butane. 1-propanol, 2-propanol, propane, propylene glycol, hexane, methanol, and 15-crown 5-ether.

The progress of the crosslinking reaction may be recognized through the analysis of a crystal structure by an oblique incidence wide-angle X-ray scattering method.

When the cyclic molecules in the plurality of pseudo-polyrotaxanes and/or polyrotaxanes are bonded in series and in parallel, the structural body in the nanosheet becomes stronger.

The method of producing a nanosheet of the embodiment of the present invention may further include a step of removing part or all of the plurality of chain polymers 20 included in part of the plurality of cyclic molecules 10 in a skewered manner as illustrated in FIG. 1E after the obtainment of the nanosheet 42 in which the cyclic molecules are crosslinked to each other in FIG. 1D.

A method of removing the chain polymers 20 from the cyclic molecules 10 is known. See, for example, Langmuir 2013, 29, 5939-5943 (https://pubs.acs.org/doi/10.1021/la400478d). In the literature, there is a description that composite particles in each of which polyethylene glycol (PEG) is included in crosslinked α-CD are dispersed in chloroform, and free crosslinked CD particles are obtained by centrifugation through utilization of a difference in solubility in chloroform between crosslinked CD particles (each having low solubility) and the PEG (having high solubility). The chain polymers 20 can be removed from the cyclic molecules 10 by performing the following washing step once or twice or more: the nanosheet in which the cyclic molecules are crosslinked to each other is dispersed in, for example, water or an organic solvent typified by chloroform, ethanol, acetone, hexane, or the like; and the dispersed product is centrifuged, and the supernatant is removed and dispersed in a polar solvent again.

In the nanosheet of the embodiment of the present invention, the cyclic molecules in the nanosheet 42 are crosslinked to each other. Accordingly, even when the step of removing the chain polymers 20 from the cyclic molecules 10 is performed, the structures of the crosslinked cyclic molecules are maintained.

In a nanosheet 44 obtained by removing the chain polymers 20 from the cyclic molecules 10, the amount of the chain polymers 20 in the nanosheet 44 is reduced, or the polymers are completely removed. Accordingly, the ratio of an effective space, which may be used in the carrying, housing, and adsorption of a target molecule, in each of spaces in a cavity formed by the one cyclic molecule 10, and a column defined and formed by the plurality of cyclic molecules 10 in the nanosheet 44 increases. Accordingly, the function of the nanosheet 44 having such configuration of carrying the target molecule, the surface adhesion property of the target molecule (substance to be adsorbed) derived from the nanosheet structure, and the like can be further improved.

The production method of the embodiment of the present invention may optionally include a step for the introduction of one or more of the second cyclic molecules, the first substance, the second substance, and the third substance described above into the nanosheet 42 or 44.

The nano or microstructural body has been described above by being embodied as a nanosheet for facilitating the understanding of the invention. However, the nano or microstructural body of the present invention may be a nano or microstructural body except a nanosheet.

Figure 2:
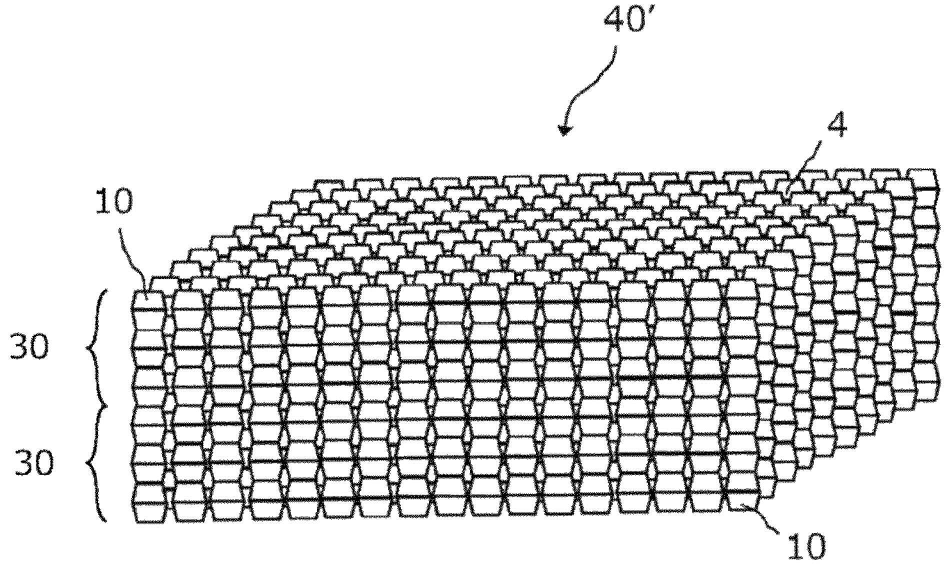
FIG. 2 is a schematic perspective view of a nano or microstructural body of another embodiment of the present invention.

FIG. 2 is an illustration of an example of such nano or microstructural body. A nano or microstructural body 40' of one embodiment of the present invention includes the plurality of pseudo-polyrotaxanes and/or polyrotaxanes 30. The pseudo-polyrotaxanes and/or polyrotaxanes 30 each include the chain polymer 20 included in the cavity of the cyclic molecule 10 in a skewered manner, and at least part of the plurality of pseudo-polyrotaxanes and/or polyrotaxanes 30 are arranged in series with each other. In addition, another part of the plurality of pseudo-polyrotaxanes and/or polyrotaxanes 30 are arranged in parallel with each other. The plurality of pseudo-polyrotaxanes and/or polyrotaxanes 30 are arranged in each of the thickness direction of the sheet of the nano or microstructural body 40' and two directions perpendicular to the thickness direction of the sheet. Specifically, in the figure, the two pseudo-polyrotaxanes and/or polyrotaxanes 30 are arranged in series, and 17×10 pairs of the pseudo-polyrotaxanes and/or polyrotaxanes 30 are arranged in parallel.

The phrase "the plurality of pseudo-polyrotaxanes and/or polyrotaxanes are arranged in series with each other" means that the plurality of pseudo-polyrotaxanes and/or polyrotaxanes are arranged in a stacked manner in the axial directions of their cyclic molecules. The pseudo-polyrotaxanes and/or polyrotaxanes arranged in series with each other, and the other pseudo-polyrotaxanes and/or polyrotaxanes are preferably in such a relationship that their axial directions substantially coincide with each other, and their cyclic molecules are arranged substantially in one row. However, as long as the cyclic molecules are arranged in a stacked manner in the axial directions of the cyclic molecules, the positions of the individual cyclic molecules may shift in a direction perpendicular to the axial directions to some extent.

The phrase "the plurality of pseudo-polyrotaxanes and/or polyrotaxanes are arranged in parallel with each other" means that the plurality of pseudo-polyrotaxanes and/or polyrotaxanes are arranged substantially parallel to each other. It is preferred that the axial directions of the pseudo-polyrotaxanes and/or polyrotaxanes arranged in parallel with each other, and the other pseudo-polyrotaxanes and/or polyrotaxanes be substantially parallel to each other.

Although the size of the nano or microstructural body 40' is not particularly limited, dimensions in the a-axis, b-axis, and c-axis directions of the crystal of the nano or microstructural body 40' are typically of the order of nanometers (1 nm or more and less than 1,000 nm) or micrometers (1 μm or more and less than 1,000 μm). Pharmacokinetic behavior in a body varies depending on the particle size of the nano or microstructural body 40'. For example, when the particle size is equal to or more than 2 mm, the structural body is taken in a liver cell, when the particle size is equal to or more than 300 nm to 400 nm, the structural body is captured and discharged by a macrophage, when the particle size is equal to or more than 200 nm, the structural body is treated in a spleen, and when the particle size is equal to or more than 100 nm, the structural body passes a space between vascular endothelial cells. Accordingly, the nano or microstructural body 40' can be designed by selecting the size of the nano or microstructural body 40' in accordance with purposes. Herein, the structural body 1 whose dimension along at least one of the a-axis, the b-axis, or the c-axis is 1 μm or more is sometimes referred to as "microstructural body."

The nano or microstructural body may adopt any one of the following shapes: a rod shape whose length in the c-axis direction is longer than its lengths in the a- and b-axis directions; a cube shape whose length in the c-axis direction is substantially equal to its lengths in the a- and b-axis directions; and a sheet shape whose length in the c-axis direction is shorter than its lengths in the a- and b-axis directions. In addition, when the structural body has a sheet shape, the shape of the sheet in plan view may be a substantially square shape, a substantially rectangular shape, a rhombus, or a polygon (having 3, 4, 5, 6, or more sides). Further, the nano or microstructural body may adopt any one of a tent shape, that is, a hollow pyramid shape, a polyhedral shape, a columnar shape (a prism shape or a cylindrical shape; including a solid or hollow shape), and a spherical shape (including a solid or hollow shape).

When the nano or microstructural body has a rod shape, its thickness (length in the c-axis direction) is preferably 100 nm or more, more preferably from 100 nm to 1,000 μm, still more preferably from 200 nm to 100 μm, and its length in each of the a-axis and b-axis directions is preferably 50 nm or more, more preferably from 50 nm to 100 μm, still more preferably from 100 nm to 10 μm.

When the nano or microstructural body has a cube shape, its thickness (length in the c-axis direction) is preferably 50 nm or more, more preferably from 50 nm to 1,000 μm, still more preferably from 100 nm to 100 μm.

When the nano or microstructural body has a sheet shape, its thickness (length in the c-axis direction) is preferably 50 nm or more, more preferably from 50 nm to 100 μm, still more preferably from 100 nm to 10 μm, and its length in each of the a-axis and b-axis directions is preferably 100 nm or more, more preferably from 100 nm to 1,000 μm, still more preferably from 200 nm to 100 μm.

The structure of the nano or microstructural body may be appropriately controlled by changing the molecular weight, hydrophilicity and hydrophobicity, topology, and polymer blocks of each of the chain molecules.

The cyclic molecules 10 and the chain polymers 20 are as described for the method of producing a nanosheet illustrated in FIG. 1.

Examples of the cyclic molecules 10 include, but not limited to, a cyclodextrin (e.g., α-cyclodextrin, β-cyclodextrin, or γ-cyclodextrin), a crown ether, a pillararene, a calixarene, a cyclophane, a cucurbituril, and derivatives thereof. Examples of the derivatives include, but not limited to, methylated α-cyclodextrin, methylated β-cyclodextrin, methylated γ-cyclodextrin, hydroxypropylated α-cyclodextrin, hydroxypropylated β-cyclodextrin, and hydroxypropylated γ-cyclodextrin.

The weight-average molecular weight of the chain polymer 20 is preferably from 2,000 to 200,000, more preferably from 4,000 to 100,000, still more preferably from 6,000 to 50,000.

In one preferred embodiment, the chain polymer 20 is water-soluble, and examples thereof include at least one kind selected from the group consisting of: polyethylene oxide (polyethylene glycol); polypropylene oxide (polypropylene glycol); polyvinyl alcohol; polyethyleneimine; polyacrylic acid; polymethacrylic acid; polyacrylamide; cellulose derivatives such as hydroxypropylcellulose; and polyvinylpyrrolidone. Of those, at least one kind selected from the group consisting of: polyethylene glycol; and polypropylene glycol is more preferred.

The weight-average molecular weight of the water-soluble chain polymer 20 is preferably from 200 to 200,000, more preferably from 200 to 50,000, still more preferably from 200 to 20,000.

The chain polymer 20 may be a polymer having a moiety formed by the polymerization of one kind of monomer, or formed only of such moiety, may be a polymer having a copolymer formed by the polymerization of two kinds of monomers, or formed only of such copolymer moiety, or may be a polymer having a terpolymer formed by the polymerization of three kinds of monomers, or formed only of such terpolymer moiety. Examples of those moieties include the examples described above as the skeleton for forming the repeating structure. In particular, examples of those moieties include, but not limited to, at least one kind selected from the group consisting of: polyethylene glycol; polyisoprene; polyisobutylene; polybutadiene; polypropylene glycol; polytetrahydrofuran; polydimethylsiloxane; polyethylene; polypropylene; polyvinyl alcohol; and polyvinyl methyl ether.

The chain polymer 20 may be a block copolymer including two blocks. In addition, the chain polymer 20 may be a block copolymer including three blocks. When both the ends of the chain polymer 20 are housed in a column formed of the plurality of cyclic molecules 10, the adjacent cyclic molecules 10 of the adjacent pseudo-polyrotaxanes and/or polyrotaxanes can be arranged in series by a noncovalent bond interaction therebetween. In order that both the ends of the chain polymer 20 may be housed in the column formed of the plurality of cyclic molecules 10, it is preferred that no hydrophilic PEO blocks be arranged at both the ends of the chain polymer 20, or even when the hydrophilic PEO blocks are arranged, their lengths be 0.20 nm or less.

Preferred examples of the chain polymer 20 include, but not limited to, a single block polymer formed of polyethylene oxide (PEO), a diblock copolymer having a block formed of polyethylene oxide (PEO) and a block formed of polypropylene oxide (PPO), and a triblock copolymer having a block formed of polyethylene oxide (PEO), a block formed of polypropylene oxide (PPO), and a block formed of polyethylene oxide (PEO) in the stated order. The triblock copolymer formed of PEO-PPO-PEO is preferred because the PPO has hydrophobicity higher than that of the PEO, and hence the top of the PPO is more selectively included in the cyclic molecules in an aligned manner.

When the chain polymer 20 is a block copolymer, the chain length of a moiety of the chain polymer 20 included in the cyclic molecule 10 is preferably longer than the thickness of the cyclic molecule 10.

The chain polymer 20 may have an ionizable group that ionizes in water or an aqueous solution. In one preferred embodiment, the chain polymer 20 has the ionizable group at at least one terminal thereof or in the vicinity of the end. In another preferred embodiment, the chain polymer 20 has the ionizable group at at least one terminal thereof. In another preferred embodiment, the chain polymer 20 has the ionizable group at each of both terminals thereof.

The chain polymer 20 may have a non-ionizable group instead of the ionizable group. A conventionally known method may be used for the introduction of the ionizable group or the non-ionizable group into the chain polymer. The ionizable group and the non-ionizable group are as described for the embodiment of the nanosheet. Description is given by taking, as an example, a nano or microstructural body in which the cyclic molecules 10 are each γ-cyclodextrin (hereinafter "γ-CD") and the chain polymers 20 are each polyethylene oxide (PEO).

Figures 3A, 3B, 3C, 3D:
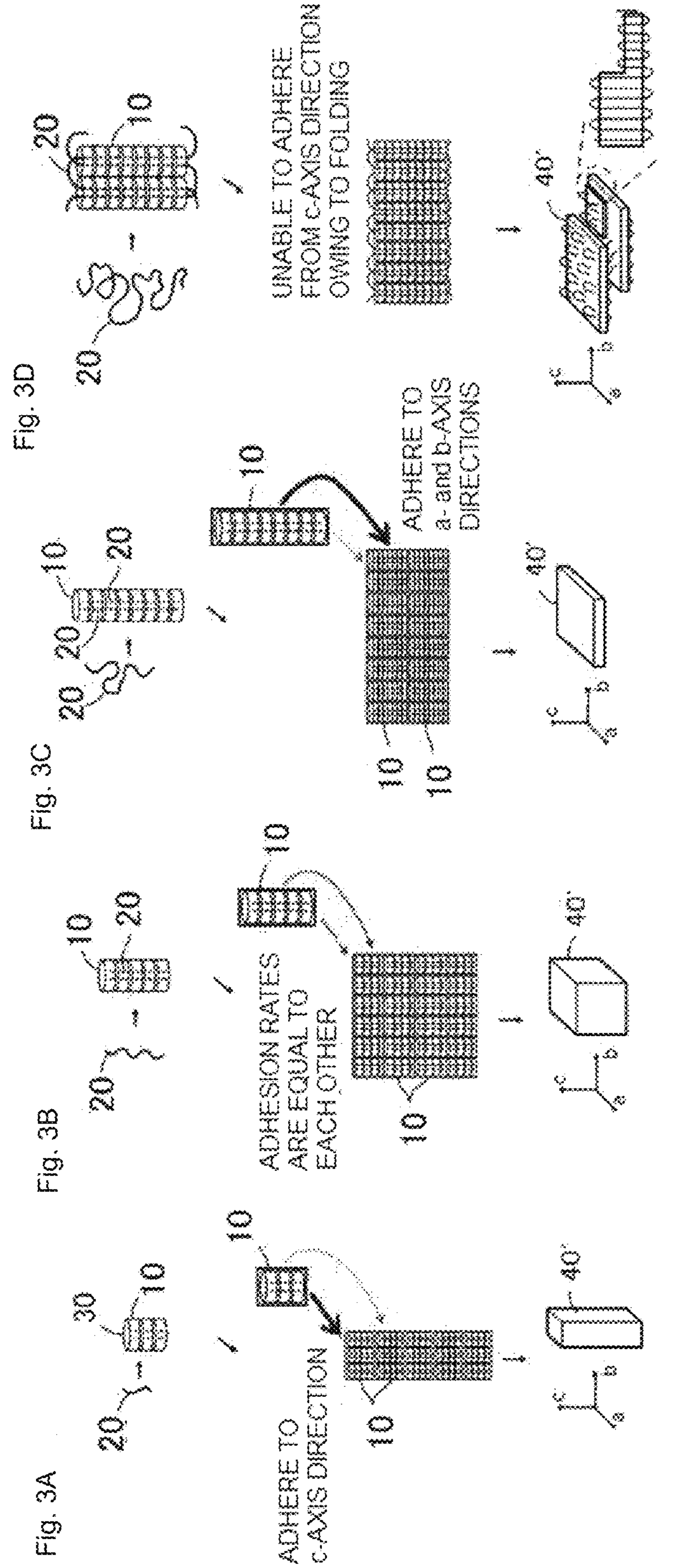
FIG. 3A, FIG. 3B, FIG. 3C, and FIG. 3D are each a schematic view for illustrating a relationship between the molecular weight of a chain polymer and the shape of a structural body.

First, with regard to the effect of the molecular weight of each of the chain polymers, the dependence of the crystal growth of the nano or microstructural body on the length of a PEO axis is summarized in FIG. 3A to FIG. 3C. When the chain polymer 20 is PEO, each of the cyclic molecules 10 forms a double-chain composite with the chain polymer 20.

When the chain polymer 20 has a small molecular weight and a short axis as illustrated in FIG. 3A, a rod-shaped nano or microstructural body in which the pseudo-polyrotaxanes and/or polyrotaxanes 30 are stacked long in a c-axis direction, that is, a direction parallel to the main axis of the chain polymer 20 is formed. In other words, the foregoing means that the crystal growth of the cyclic molecule 10 in the c-axis direction is faster than the crystal growth thereof in each of a-axis and b-axis directions perpendicular to the c-axis. In contrast, as the axis of the chain polymer 20 becomes longer, the side surface length of the nano or microstructural body in the c-axis direction becomes shorter. The foregoing means that in the longer chain polymer 20, the crystal growth of the cyclic molecule 10 along each of the a-axis and the b-axis is faster than that along the c-axis. It is assumed that when the lengths of the pseudo-polyrotaxanes and/or polyrotaxanes 30 are short, their interaction in a lateral direction is weaker than between the longer pseudo-polyrotaxanes and/or polyrotaxanes 30, and hence the pseudo-polyrotaxanes and/or polyrotaxanes 30 extend in the c-axis direction.

In an example illustrated in FIG. 3B, when the length of the chain polymer 20 is made longer than that in FIG. 3A, the interaction in the lateral direction becomes larger than that in FIG. 3A, and hence a cube-shaped nano or microstructural body whose length in the c-axis direction, and lengths in the a-axis and b-axis directions are equal to each other is formed.

In an example illustrated in FIG. 3C, when the length of the chain polymer 20 is made even longer than that in FIG. 3B, a sheet-shaped nano or microstructural body that is longer in each of the a-axis and b-axis directions than in the c-axis direction is formed.

When the length of the chain polymer 20 is made even longer than that in FIG. 3C, as illustrated in FIG. 3D, the chain polymer 20 starts to bend, and a bent site of the chain polymer 20 inhibits the crystal growth of the cyclic molecule 10 along the c-axis. Thus, a sheet-shaped nano or microstructural body is formed. A portion including the bent site of the chain polymer 20 protrudes from the cyclic molecule 10. When the length or molecular weight of the chain polymer 20 is changed as described above, the behavior of the crystal of the nano or microstructural body formed by the cyclic molecule 10 can be controlled.

Next, the effects of the hydrophilicity and hydrophobicity of the chain polymer 20 are described. When the cyclic molecule 10 is γ-CD and the chain polymer 20 is PEO, as described above, nano or microstructural bodies of various shapes are formed along with a change in molecular weight of the chain polymer. In contrast, when polypropylene oxide (PPO) that is hydrophobic is used instead of the PEO that is hydrophilic as the chain polymer 20, the shape of the nano or microstructural body changes as follows as the chain polymer 20 becomes longer: from a rod shape whose length in the c-axis direction is longer than its lengths in the a- and b-axis directions, to a cube shape whose length in the c-axis direction is substantially equal to its lengths in the a- and b-axis directions, to a sheet shape whose length in the c-axis direction is shorter than its lengths in the a- and b-axis directions, and to a random (disordered) shape. As described above, the hydrophilicity and hydrophobicity of the chain polymer 20 may also affect the behavior of the crystal of the nano or microstructural body.

Without wishing to be bound by any theory, the above-mentioned phenomenon may be interpreted as follows: when the chain polymer 20 is hydrophilic, hydration occurs on the surface of the nano or microstructural body to stabilize the structure thereof; and in contrast, when the chain polymer 20 is hydrophobic, its hydrophobic aggregation competes with the crystallization of γ-CD to make the structure disordered.

Figure 4A:
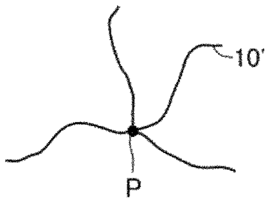
FIG. 4A is a schematic view of a branched PEO.
Figure 4B:
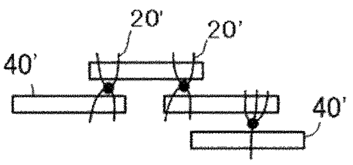
FIG. 4B is a schematic view of the sheet of a structural body using the branched PEO of FIG. 4A.
Figure 4C:
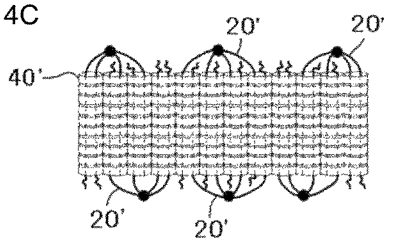
FIG. 4C is a schematic view for illustrating the linked state of the sheet of FIG. 4B.

Next, the effect of the topology of the chain polymer 20 is described. When the chain polymer 20 is single-chain PEO, as described above, structural bodies of various shapes are formed along with a change in molecular weight of the polymer. In contrast, when PEO having a branching portion P illustrated in FIG. 4A is used as a chain polymer 20', as illustrated in FIG. 4B, the branching portion P suppresses the crystal growth of the cyclic molecule, and hence a sheet-shaped nano or microstructural body 40' having a uniform thickness is formed. However, as illustrated in FIG. 4C, the chain polymer 20' serves as a bridge to link the sheets. As described above, the topology of the chain polymer 20 may affect the behavior of the crystal of the nano or microstructural body.

Figure 5A:
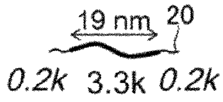
FIG. 5A, FIG. 5B, FIG. 5C, FIG. 5D, FIG. 5E, and FIG. 5F are views for illustrating a relationship between the order in which γ-CD is chemically bonded to portions (segments) in the chain polymer different from each other in composition and the shape of a structural body.
Figure 5B:
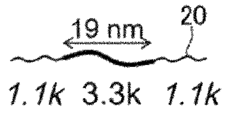
Figure 5C:
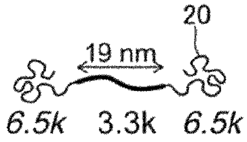
Figure 5D:
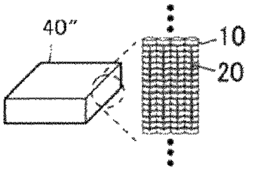
Figure 5E:
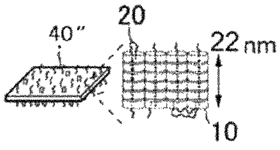
Figure 5F:
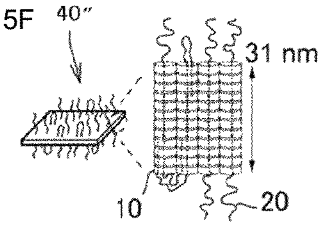

Next, the effect of a change in configuration of the polymer blocks of the chain polymer is described. For example, triblock polymers illustrated in FIG. 5A to FIG. 5C in each of which a central block is a PPO having a molecular weight of 3.3k (the symbol "k" means kilo, and the same holds true for the following), and blocks on both of its sides are each a PEO having a molecular weight of 0.2k, 1.1k, or 6.5k are each used as the chain polymer 20. In this case, block structural bodies 40" illustrated in FIG. 5D to FIG. 5F, the structural bodies serving as nano or microstructural bodies, are formed, respectively. In each case, with regard to the intensity of an interaction with γ-CD, an interaction between γ-CD and the PPO is stronger than an interaction between γ-CD and the PEO, and hence γ-CD is localized to the center of the chain polymer 20 in its axial direction. When the localization is utilized, in the case where the hydrophobic PPO block is arranged at the center of the chain polymer, the hydrophilic PEO blocks are arranged at both the ends thereof, and the lengths of the PEO blocks are made sufficiently long, the PEO blocks at both the ends of the chain polymer 20 protrude from a column formed of a plurality of γ-CD molecules, and hence a single-layer sheet having a single thickness, in other words, a sheet in which one pseudo-polyrotaxane and/or polyrotaxane is arranged in its thickness direction can be produced.

The nano or microstructural body 40' may further include a component except the pseudo-polyrotaxanes and/or polyrotaxanes 30, that is, an additional substance 60 (illustrated in FIG. 6A) except the above-mentioned cyclic molecules 10 and the above-mentioned chain polymers 20 included in the cavities of the cyclic molecules 10 in a skewered manner.

Figure 6A:
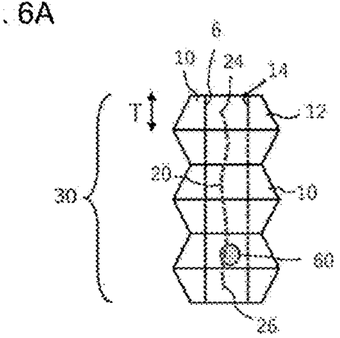
FIG. 6A is a schematic front view of a pseudo-polyrotaxane whose chain polymer is polypropylene oxide (PPO)

The substance 30 may be bonded to the cyclic molecule 10, may be bonded to the chain polymer 20, may be held in a space 4 between the plurality of pseudo-polyrotaxanes and/or polyrotaxanes 30 (i.e., when a plurality of, in particular, 2, 3, or 4 columns that are columnar structures formed of the pseudo-polyrotaxanes and/or polyrotaxanes are present, a space therebetween) (illustrated in FIG. 2), may be housed in the cavity 14 defined and formed by the one cyclic molecule 10, or may be housed in a space 6 defined and formed by the plurality of cyclic molecules 10 (illustrated in FIG. 6A). When the substance 60 is bonded to the chain polymer 20, the substance is preferably bonded to each of both the ends, or one end, of the chain polymer 20, or the vicinity of the end, but may be bonded to another site of the chain polymer 20. In addition, to house the substance 60 in the space 6 defined and formed by the plurality of cyclic molecules 10, the chain polymer 20 is preferably not housed therein, but a molecule except the substance 60 typified by the chain polymer 20 may be housed therein.

The size of the space 4 between the plurality of pseudo-polyrotaxanes and/or polyrotaxanes 30, the size of the cavity 14 defined and formed by the one cyclic molecule 10, and the size of the space 6 defined and formed by the plurality of cyclic molecules 10 may be appropriately changed by changing, for example, the kind of the cyclic molecule 10, the length of the chain polymer 20, and the hydrophilicity and hydrophobicity of the chain polymer 20. Accordingly, the size of the space 4, the size of the cavity 14, and/or the size of the space 6 only needs to be appropriately changed in accordance with the size of the substance 60 that is wished to be housed.

The nano or microstructural body 40' of this embodiment is thicker than the related-art single-layer nanosheet, and hence a large amount of the substance 60 such as a drug can be taken in the one structural body. Accordingly, the nano or microstructural body 40' of this embodiment can function as a vehicle for the drug to enable the lengthening of the sustained release time of the drug.

Further, the nano or microstructural body 40' of this embodiment includes a molecule having high biosafety, and is hence suitable for utilization in a living organism.

In addition, when the nano or microstructural body 40' of this embodiment is produced by using the short chain polymer 20 as a raw material, the production can be performed more rapidly, and energy and cost can be reduced.

As illustrated in FIG. 6A to FIG. 6F, the cyclic molecules 10 and the chain polymers 20 in the nano or microstructural body 40' may each adopt various configurations to the extent that an intended function of the nano or microstructural body 40' can be exhibited as long as a structure as an assembly called the nano or microstructural body 40' is maintained.

For example, in FIG. 6A, the plurality of (six in the figure) cyclic molecules 10 form a column, and the one chain polymer 20 is housed in the space 6 formed by the continuation of the cavities 14 of the cyclic molecules 10. The one chain polymer 20 extends over the cavities 14 of the plurality of cyclic molecules 10, but both the ends of the chain polymer 20 do not reach both ends of the column formed of the plurality of cyclic molecules 10 but are housed in the space 6. The column formed of the plurality of cyclic molecules 10 may also be called a laminate formed of the plurality of cyclic molecules 10, that is, a stack. The substance 60 may be housed in the cavities 14 of the cyclic molecules 10 or the space 6 formed by the plurality of cyclic molecules 10, or may not be housed therein.

Figure 6B:
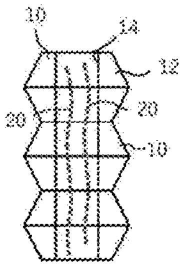
FIG. 6B is a schematic front view of a pseudo-polyrotaxane whose chain polymer is polyethylene oxide (PEO)

In FIG. 6B, the two chain polymers 20 are housed in the space 6, and the two chain polymers 20 extend across the cavities 14 of the plurality of cyclic molecules 10. Both the ends of each of the chain polymers 20 reach both the ends of the column formed of the plurality of cyclic molecules 10, and hence the total height of the plurality of cyclic molecules 10 for forming the one pseudo-polyrotaxane and/or polyrotaxane 2 substantially corresponds to the total length of the chain polymer 20.

Figure 6C:
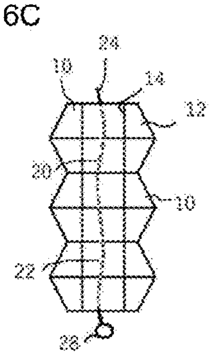
FIG. 6C is a schematic front view of a pseudo-polyrotaxane whose chain polymer extends from one end of a column formed of a series of cyclic molecules to the other end thereof.

In FIG. 6C, both the ends of the chain polymer 20 slightly protrude from the cyclic molecules 10 to the outside. One end of a main body 22 of the chain polymer 20 has a modifying group 28.

Figure 6D:
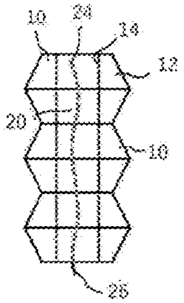
FIG. 6D is a schematic front view of a pseudo-polyrotaxane whose chain polymer extends beyond the lower end of a column formed of six cyclic molecules, but does not extend up to the upper end thereof.

In FIG. 6D, one end 24 of the chain polymer 20 is housed in the space 6, and another end 26 thereof slightly protrudes from the cyclic molecules 10 to the outside.

Figure 6E:
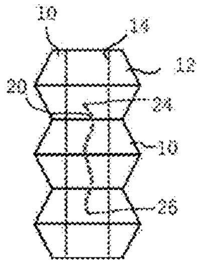
FIG. 6E is a schematic front view of a pseudo-polyrotaxane whose chain polymer reaches none of the upper end and the lower end of a column formed of six cyclic molecules.

In FIG. 6E, the one chain polymer 20 is housed in the space 6, and such chain polymer 20 extends to the cavities 14 of the four cyclic molecules 10 but does not extend to the cavities 14 of the top and bottom cyclic molecules 10. That is, the length of the chain polymer 20 is short, and is a half or less of the length of the space 6 (i.e., the total height of the plurality of cyclic molecules 10).

Figure 6F:
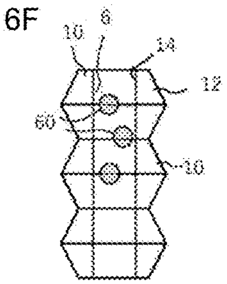
FIG. 6F is a schematic front view for illustrating a series of cyclic molecules free of any chain polymer.

In FIG. 6F, only the column formed of the plurality of cyclic molecules 10 is present, and the chain polymer 20 is absent. In this embodiment, the substance 60 is housed in the space 6 formed by the plurality of cyclic molecules 10.

In one preferred embodiment, all of the columns each formed of the plurality of cyclic molecules 10 in the nano or microstructural body 40' each include the chain polymer 20. In another preferred embodiment, part of the columns each formed of the plurality of cyclic molecules 10 in the nano or microstructural body 40' each include the chain polymer 20, and the other part of the columns are each free of the chain polymer 20.

As described above, the size of the space 4, the size of the cavity 14, and/or the size of the space 6 may be appropriately designed and adjusted in accordance with the size of the substance 60 that is wished to be housed. In addition, the occupancy of the size of the space 4, the size of the cavity 14, and/or the size of the space 6 in the nano or microstructural body 40' may be appropriately designed and adjusted. Accordingly, for example, when the substance 60 is a drug, the drug is housed in a desired amount in the space 4, cavity 14, and/or space 6 of the nano or microstructural body 40', and hence the nano or microstructural body 40' can be caused to function as a drug-encapsulated body or a drug release-controlling carrier.

The amount of the substance 60 in the nano or microstructural body 40' may be measured by absorbance measurement. For example, the substance concentration-absorbance calibration curve of a solution, which is obtained by dissolving the substance 60 at a known concentration in a solvent, at a predetermined wavelength is measured in advance. A predetermined amount of the nano or microstructural body 40' is dissolved in the same solvent, and the absorbance of the solution is measured, followed by the determination of the absorbance value thereof at the predetermined wavelength. The concentration of the substance is calculated from the determined absorbance value and the calibration curve, and the amount of the substance 60 in the nano or microstructural body 40' is calculated. In a certain embodiment, the amount of the substance 60 in the nano or microstructural body 40' is 0.0001 mass % or more, and may be more specifically, but not limited to, from 0.001 mass % to 11 mass %. In the case of the substance 60 in the nano or microstructural body 40' or the substance 60 to be encapsulated in the nano or microstructural body 40', the substance 60 comprehends the substance 60 housed in the space 6 defined and formed by the cyclic molecules 10, the substance 60 that is not included in the cyclic molecule 10 but is present between the plurality of cyclic molecules 10, and the substance 60 that is not included in the cyclic molecule 10 but adheres not to a space between the plurality of cyclic molecules 10 but to the outer surface of the nano or microstructural body 40'.

Next, a method of producing the nano or microstructural body is described.

Production methods I and II for the nano or microstructural body of this embodiment are provided.

<Production Method I>

The production method I includes the steps of:

(a) preparing the cyclic molecules 10;

(b) preparing the chain polymers 20; and (c) mixing the cyclic molecules 10 and the chain polymers 20 in water or an aqueous solution. Such production method can provide a nano or microstructural body including a plurality of pseudo-polyrotaxanes and/or polyrotaxanes including the chain polymers 20 included in the cavities of the cyclic molecules 10 in a skewered manner, in which at least part of the plurality of pseudo-polyrotaxanes and/or polyrotaxanes are arranged in series with each other.

In the step (c), the plurality of pseudo-polyrotaxanes and/or polyrotaxanes including the chain polymers having both ends housed in columns formed of the plurality of cyclic molecules interact with each other, and hence at least part of the plurality of pseudo-polyrotaxanes and/or polyrotaxanes are arranged in series with each other.

The "cyclic molecules 10" and the "chain polymers 20" are as described above.

<Step (a)>

The step (a) is a step of preparing the cyclic molecules 10.

In the step, commercial cyclic molecules may be purchased, or the cyclic molecules may be prepared. When a derivative is prepared, the derivative may be obtained by, for example, a method described in Literature 1: Khan, A. R. et al., Chem Rev 1998, 98(5), 1977-1996.

<Step (b)>

The step (b) is a step of preparing the chain polymers 20 including the chain polymers 20.

Herein, the chain polymers 20 may be purchased on the market, or may be prepared. When the "chain polymers 20" are prepared, the chain polymers 20 may be obtained by, for example, methods described in the following literatures 2 to 5.

Literature 2: Hillmyer, M. A. et al., Macromolecules 1996, 29(22) 6994-7002. Literature 3: Ding, J. F. et al., Eur Polym J 1991, 27(9), 901-905. Literature 4: Allegaier, J. et al., Macromolecules 2007, 40(3), 518-525. Literature 5: Malik, M. I. et al., Eur Po. ym J 2009, 45(3), 899-910. <Step (b)> The step (a) only needs to be provided before the step (c). That is, the step (a) and the step (b) may be performed separately from each other. Whichever comes first is fine.

<Step (c)>

The step (c) is a step of mixing the cyclic molecules 10 and the chain polymers 20 in water or an aqueous solution. The water or the aqueous solution is not particularly limited as long as the water or the aqueous solution serves as a solvent capable of dissolving at least one of the cyclic molecules 10 or the chain polymers 20.

Specific examples of the water or the aqueous solution to be used in the step (c) may include, but not limited to, pure water, an aqueous solution of an alcohol, an aqueous solution of an acid, an aqueous solution of an alkali, a buffer, a culture medium, and blood plasma.

The above-mentioned nano or microstructural body can be obtained by the production method including the steps (a) to (c).

The above-mentioned production method may include a step except the steps (a) to (c). Examples of the step except the steps (a) to (c) may include, but not limited to: a step of preparing the above-mentioned "chain polymers 20," which is provided before the step (b); a step of purifying the nano or microstructural body, which is provided after the step (c); and the inclusion of the cyclic molecule and the first substance and the synthesis of pseudo-polyrotaxanes or polyrotaxanes, which may be provided before the step (b). In addition, when the nano or microstructural body has the above-mentioned substance 60, the production method of this embodiment may include a step for the introduction of the substance 60 into the nano or microstructural body.

Further, the production method desirably further includes, after the step (c), a step of modifying part of the pseudo-polyrotaxanes of the obtained nano or microstructural body.

The modifying step may be a step of introducing a first substituent into each of the chain polymers 20, for example, at an end of each of the chain polymers 20. As long as the nano or microstructural body is obtained, the first substituent may be a capping group having such a capping action as to prevent dissociation of the cyclic molecules 10, or may have any other action. The first substituent may have any combination of those actions, and may exhibit all the actions.

For example, the groups described for the group of the nanosheet having a capping action and having the action of a non-ionizable group may each be used as the group having a capping action.

A group having other action is, for example, a group having the action of an ionizable group. The groups described for the group of the nanosheet having the action of an ionizable group may each be used as such group.

The modifying step may be a step of introducing a second substituent into each of the cyclic molecules 10 as long as the structural body is obtained.

<Production Method II>

The production method II includes the steps of:

(a) preparing the cyclic molecules 10;

(b') preparing the chain polymers 20;

(c') mixing the cyclic molecules 10 and the chain polymers 20 in water or an aqueous solution to provide pseudo-polyrotaxanes;

(d) introducing substituents into both terminals of at least part of the chain polymers 20 to provide chain polymers 20;

(e) introducing capping groups into both terminals of at least part of the chain polymers 20 of the pseudo-polyrotaxanes and/or the chain polymers 20; and (f) mixing the resultant pseudo-polyrotaxanes and/or polyrotaxanes in water or an aqueous solution. Such production method can provide a structural body including a plurality of pseudo-polyrotaxanes and/or polyrotaxanes including the chain polymers 20 included in the cavities of the cyclic molecules 10 in a skewered manner, in which at least part of the plurality of pseudo-polyrotaxanes and/or polyrotaxanes are arranged in series with each other.

In the step (f), the plurality of pseudo-polyrotaxanes and/or polyrotaxanes including the chain polymers having both ends housed in columns formed of the plurality of cyclic molecules interact with each other, and hence at least part of the plurality of pseudo-polyrotaxanes and/or polyrotaxanes are arranged in series with each other.

Herein, the step (a) is the same as the above-mentioned "step (a)." In the step (b'), the "chain polymers 20" described in the above-mentioned step (b) may be used.

As in the above-mentioned step (c), the step (c') is a step of mixing the cyclic molecules 10 and the chain polymers 20 in the water or the aqueous solution, and is a step of obtaining the pseudo-polyrotaxanes through the mixing. As described in the step (c), the water or the aqueous solution is not particularly limited as long as the water or the aqueous solution is a solvent in which at least one of the cyclic molecules 10 or the chain polymers 20 are soluble.

Specific examples of the water or the aqueous solution to be used in the step (c) may include, but not limited to, pure water, an alcohol aqueous solution, an acid aqueous solution, an alkali aqueous solution, a buffer, a culture solution, and plasma.

The step (d) is a step of introducing the substituents into both the terminals of at least part of the chain polymers 20 to provide the chain polymers 20.

As a nonlimitative example of the introduction of the substituents described above, a carboxylic acid can be introduced by an oxidation reaction including using hypochlorous acid and 2,2,6,6-tetramethylpiperidine 1-oxyl. An amino group can be introduced by a coupling reaction including using 1,1'-carbonyldiimidazole and ethylenediamine. A sulfo group can be introduced by causing 1,3-propanesultone to react with the chain polymer 20.

Other nonlimitative examples of the introduction of the substituents include, but not limited to, a condensation reaction, such as esterification or amidation, using a condensation agent, such as 4-(4,6-dimethoxy-1,3,5-triazin-2-yl)-4-methylmorpholinium chloride (DMT/MM), N,N'-dicyclohexylcarbodiimide (DCC), 1-(3-dimethylaminopropyl)-3-ethylcarbodiimide (EDC), benzotriazol-1-yloxy-trisdimethylaminophosphonium salt (BOP), (benzotriazol-1-yloxy)tripyrrolidinophosphonium hexafluorophosphate (PyBOP), or O-(7-dibenzotriazol-1-yl)-N,N,N',N'-tetramethyluronium hexafluorophosphate (HATU), a nucleophilic substitution reaction, and an addition reaction.

The step (e) is a step of introducing the so-called capping groups, and is a step of introducing the capping groups to reduce the desorption rate of the cyclic molecule 10. A conventionally known approach may be used for the step, and the step may be, for example, a step described in Harada et al., Nature, 1992, 356, 325-327. In addition, examples of the capping groups may include capping groups that may be used for conventionally known polyrotaxanes. Examples thereof may include capping groups described in M. Okada et al., J Polym. Sci. A: Polym. Chem, 2000, 38, 4839-4849.

The present invention is more specifically described by way of Examples, but the present invention is not limited thereto.

EXAMPLES

Synthesis Example 1. Synthesis of α,ω-Bis-Amino Polyethylene Glycol-Block-Polypropylene Glycol-Block-Polyethylene Glycol A solution of α,ω-bis-hydroxy polyethylene glycol-block-polypropylene glycol-block-polyethylene glycol (Pluronic (trademark) F68; PEO76PPO29PEO76, Mw=8,400 g/mol: 1 g, 0.119 mmol) in 10 mL of tetrahydrofuran was prepared, and was dropped into a separately prepared solution of 0.212 g (1.31 mmol) of 1,1'-carbonyldiimidazole in 6.3 mL of tetrahydrofuran. The resultant solution was further stirred at room temperature overnight, and was then dropped into ethylenediamine (794 μL, 11.9 mmol). After the completion of the reaction, tetrahydrofuran was evaporated, and the resultant white solid was dissolved in water, followed by its purification by dialysis. After the purification, water was removed by freeze-drying. Thus, a target product was obtained (0.92 g, 92%).

Example 1. Preparation of Nanosheet 1.8 Grams of β-cyclodextrin was dissolved in 100 ml of ion-exchanged water, and 0.8 g of α,ω-bis-amino polyethylene glycol-block-polypropylene glycol-block-polyethylene glycol produced in Synthesis Example 1 was added to and sufficiently dissolved in the resultant aqueous solution of β-cyclodextrin. The solution was stirred as it was at room temperature for 30 days to provide an uncrosslinked nanosheet dispersion that was opaque. Next, 10 ml of a 0.1 N aqueous solution of sodium hydroxide and 1.2 mL of epichlorohydrin were added to 90 mL of the uncrosslinked nanosheet dispersion, and the mixture was stirred at room temperature for 48 hours. 10 Milliliters of 0.1 N hydrochloric acid was added to neutralize the reaction liquid, and then the neutralized product was centrifuged (at 12,000 rpm for 10 minutes) with a centrifugal separator, followed by the removal of 90 mL of the supernatant liquid. 90 Milliliters of ion-exchanged water was newly added to the remaining white solid paste to suspend the white solid, and centrifugation was performed again to remove 90 mL of the supernatant liquid. The series of steps including the addition of ion-exchanged water, the centrifugation, and the removal of the supernatant liquid was defined as a water washing step, and the water washing step was repeated four times. The washed liquid was made substantially transparent by four times of the washing step, and in the fourth step, the supernatant liquid of the centrifugation was removed to the extent possible. Thus, 2.3 g of a nanosheet dispersion-1 was obtained (the dispersion is referred to as “sample IT-162”). 100 milligrams of the sample IT-162 was collected, and was subjected to freeze-drying for 24 hours to provide 9.8 mg of a white solid. Accordingly, the concentration of the nanosheets in the sample IT-162 was calculated to be 9.8 wt %.

Example 2. Evaluation of Degradability of Nanosheet

1 Milligram of the sample IT-162 obtained in Example 1 was diluted with 1 mL of ion-exchanged water to produce a diluted nanosheet dispersion having a concentration of about 0.01 wt %.

Figure 7:
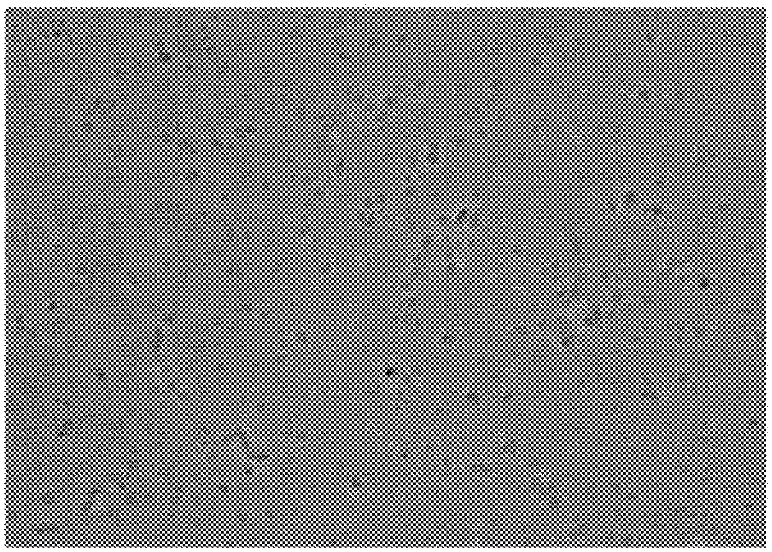
FIG. 7 is a photograph obtained by observing a liquid, which is obtained by diluting a sample IT-162 containing a nanosheet with water, with a phase-contrast microscope.

The dispersion was observed with a phase-contrast microscope. The result is shown in FIG. 7. The result suggested that even when the sample IT-162 was diluted with ion-exchanged water, a nanosheet crystal structure remained, and hence β-cyclodextrin was crosslinked.

Figure 8:
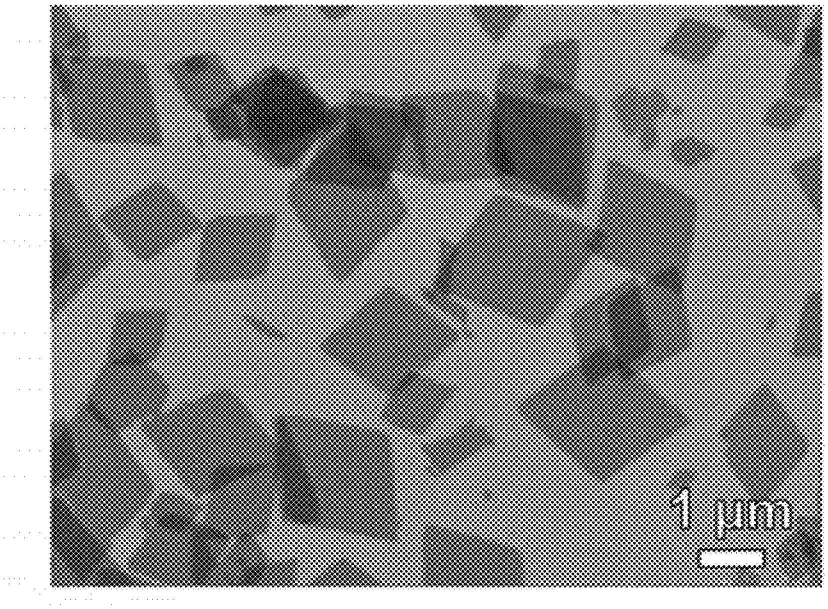
FIG. 8 is an image obtained by observing a crystal structure in the sample IT-162 with a scanning microscope.

Observation with a scanning microscope recognized that rhombic nanosheets 0.3 μm to 2 μm on a side were formed (FIG. 8).

Figure 9:
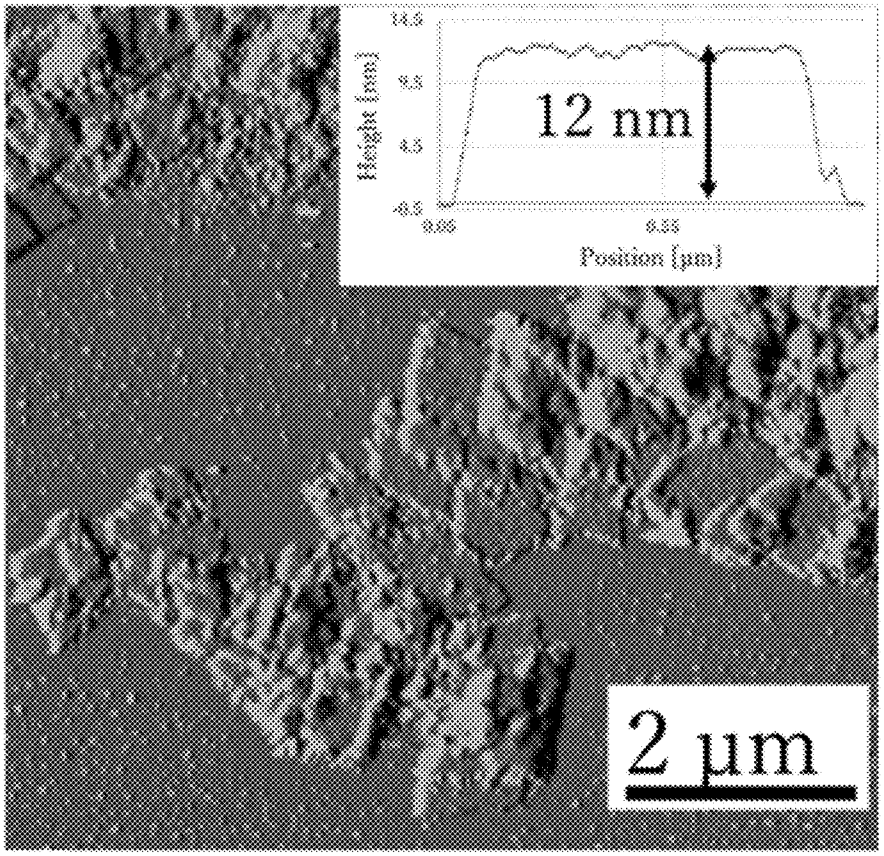
FIG. 9 is an image and a graph (inserted figure) obtained by observing the crystal structure in the sample IT-162 with an atomic force microscope.

Observation with an atomic force microscope recognized that the crystal structures in the sample IT-162 each had a thickness of 12 nm, and were hence nanosheets (FIG. 9).

Example 3. Introduction of Rhodamine B

Figure 10A:
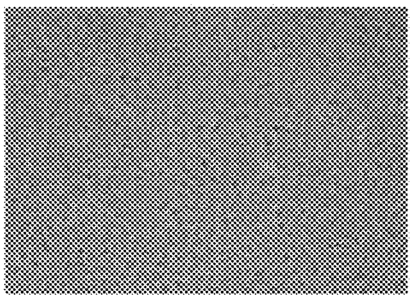
FIG. 10A is a phase-contrast microscope photograph of the diluted liquid of Example 3.
Figure 10B:
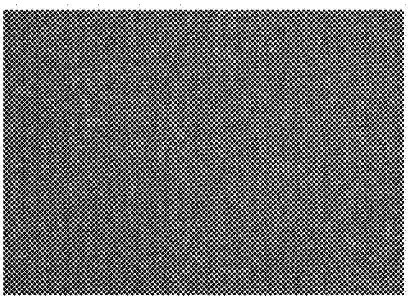
FIG. 10B is a fluorescence microscope photograph thereof.

900 Microliters of an aqueous solution (100 μg/mL) of rhodamine B was added to 50 mg of the nanosheet dispersion-1 (sample IT-162) obtained in Example 1, and the mixture was shaken at room temperature for 24 hours. The resultant solution was diluted fivefold with ion-exchanged water, and was observed with a phase-contrast microscope and a fluorescence microscope. The results are shown in FIG. 10A and FIG. 10B, respectively. The crystal structures of nanosheets were able to be observed with the phase-contrast microscope. In addition, fluorescent coloring was observed in each of the crystal structures with the fluorescence microscope, and hence it was shown that rhodamine B was introduced into each of the nanosheets.

Example 4. Introduction of Donepezil Hydrochloride

700 Microliters of an aqueous solution (500 μg/mL) of donepezil hydrochloride was added to 500 mg of the nanosheet dispersion-1 (sample IT-162) obtained in Example 1, and the mixture was shaken at room temperature for 48 hours. The nanosheet dispersion having introduced thereinto donepezil hydrochloride was centrifuged (at 12,000 rpm for 10 minutes), and the supernatant liquid was collected.

The amount of donepezil hydrochloride introduced into the nanosheets was determined by an absorbance measurement method based on a spectrophotometer. That is, the concentration-absorbance calibration curve of an aqueous solution of donepezil hydrochloride at a predetermined wavelength (λ=320 nm) was produced in advance, and the absorbance value of the supernatant liquid of the centrifugation described above after the introduction was determined, and the concentration of donepezil hydrochloride in the liquid was also determined from the calibration curve. A reduction in concentration before and after the introduction of donepezil hydrochloride was defined as the amount of donepezil hydrochloride introduced into the nanosheets. The concentration of donepezil hydrochloride in the nanosheet dispersion before the introduction was defined as 304 μg/mL in consideration of dilution with a moisture amount in the nanosheet dispersion. As a result, the concentration of donepezil hydrochloride in the nanosheet dispersion after the introduction was found to be 0 μg/mL by absorbance measurement. Accordingly, 304 μg/mL of donepezil hydrochloride was introduced into 43 mg/ml of the nanosheets, and hence the introduction amount of donepezil hydrochloride accounted for 0.70 wt % of the weight of the nanosheets.

Example 5. Introduction of 5-Fluorouracil

700 Microliters of an aqueous solution (300 μg/mL) of 5-fluorouracil was added to 500 mg of the nanosheet dispersion-1 obtained in Example 1, and the mixture was shaken at room temperature for 48 hours. The nanosheet dispersion having introduced thereinto 5-fluorouracil was centrifuged (at 12,000 rpm for 10 minutes), and the supernatant liquid was collected.

The introduction amount of 5-fluorouracil was determined by the same process as that of Example 4 except that a concentration-absorbance calibration curve was produced at a predetermined wavelength (λ=270 nm). As a result, the concentration of 5-fluorouracil before the introduction was 183 μg/mL, and the concentration of 5-fluorouracil after the introduction was found to be 138 μg/mL by absorbance measurement. Accordingly, 45 μg/mL of 5-fluorouracil was introduced into 43 mg/mL of the nanosheets, and hence the introduction amount of 5-fluorouracil accounted for 0.10 wt % of the weight of the nanosheets.

Example 6. Introduction of Hydrocortisone

700 Microliters of an aqueous solution (100 μg/mL) of hydrocortisone was added to 500 mg of the nanosheet dispersion-1 obtained in Example 1, and the mixture was shaken at room temperature for 48 hours. The nanosheet dispersion having introduced thereinto hydrocortisone was centrifuged (at 12,000 rpm for 10 minutes), and the supernatant liquid was collected.

The introduction amount of hydrocortisone was determined by the same process as that of Example 4 except that a concentration-absorbance calibration curve was produced at a predetermined wavelength (λ250 nm). As a result, the concentration of hydrocortisone before the introduction was 61 μg/mL, and the concentration of hydrocortisone after the introduction was found to be 26 μg/mL by absorbance measurement. Accordingly, 35 μg/mL of hydrocortisone was introduced into 43 mg/mL of the nanosheets, and hence the introduction amount of hydrocortisone accounted for 0.08 wt % of the weight of the nanosheets.

Example 7. Introduction of Betamethasone

500 Microliters of an aqueous solution (30 μg/mL) of betamethasone was added to 100 mg of the nanosheet dispersion-1 obtained in Example 1, and the mixture was shaken at room temperature for 48 hours. The nanosheet dispersion having introduced thereinto betamethasone was centrifuged (at 12,000 rpm for 10 minutes), and the supernatant liquid was collected.

The introduction amount of betamethasone was determined by the same process as that of Example 4 except that a concentration-absorbance calibration curve was produced at a predetermined wavelength (λ=250 nm). As a result, the concentration of betamethasone before the introduction was 25 μg/mL, and the concentration of betamethasone after the introduction was found to be 17 μg/mL by absorbance measurement. Accordingly, 8 g/mL of betamethasone was introduced into 17 mg/ml of the nanosheets, and hence the introduction amount of betamethasone accounted for 0.05 wt % of the weight of the nanosheets.

Example 8. Introduction of Menadione

500 Microliters of an aqueous solution (30 μg/mL) of menadione was added to 100 mg of the nanosheet dispersion-1 obtained in Example 1, and the mixture was shaken at room temperature for 48 hours. The nanosheet dispersion having introduced thereinto menadione was centrifuged (at 12,000 rpm for 10 minutes), and the supernatant liquid was collected.

The introduction amount of menadione was determined by the same process as that of Example 4 except that a concentration-absorbance calibration curve was produced at a predetermined wavelength (λ=250 nm). As a result, the concentration of menadione before the introduction was 25 μg/mL, and the concentration of menadione after the introduction was found to be 10 μg/mL by absorbance measurement. Accordingly, 15 μg/ml of menadione was introduced into 17 mg/ml of the nanosheets, and hence the introduction amount of menadione accounted for 0.09 wt % of the weight of the nanosheets.

The introduction of the compounds into the nanosheets is summarized in Table 1 for Example 4 to Example 8.

TABLE 1

| Example | Introduced compound | Nanosheet concentration (mg/mL) | Concentration of introduced compound (μg/mL) Before introduction | After introduction | Weight of introduced compound/weight of nanosheets |
|---|---|---|---|---|---|
| Example 4 | Donepezil hydrochloride | 43 | 304 | 0 | 0.60% |
| Example 5 | 5-Fluorouracil | 43 | 183 | 138 | 0.10% |
| Example 6 | Hydrocortisone | 43 | 61 | 26 | 0.08% |
| Example 7 | Betamethasone | 17 | 25 | 17 | 0.05% |
| Example 8 | Menadione | 17 | 25 | 10 | 0.09% |

Comparative Example 1. Preparation of Nanosheet 1.8 Grams of β-cyclodextrin was dissolved in 100 mL of ion-exchanged water, and 0.8 g of α,ω-bis-amino polyethylene glycol-block-polypropylene glycol-block-polyethylene glycol produced in Synthesis Example 1 was added to and sufficiently dissolved in the resultant aqueous solution of β-cyclodextrin. The solution was stirred as it was at room temperature for 30 days to provide an uncrosslinked nanosheet dispersion that was opaque (the dispersion is referred to as "sample IT-142"). Next, 100 mL of the sample IT-142 was repeatedly washed with water through use of a centrifugal separator under the same conditions as those of Example 1. When the washing was performed four times, the white solid paste sedimented by centrifugation disappeared, and no nanosheet crystal structure remained (no data is shown).

Comparative Example 2. Introduction of Rhodamine B

Figure 11A:
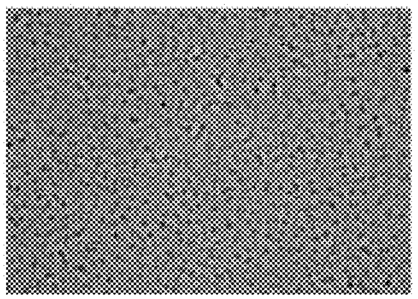
FIG. 11A is a phase-contrast microscope photograph of the diluted liquid of Comparative Example 2.
Figure 11B:
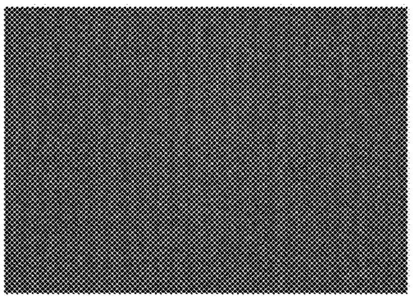
FIG. 11B is a fluorescence microscope photograph thereof.

100 Microliters of an aqueous solution (1,000 μg/mL) of rhodamine B was added to 90 mL of the uncrosslinked nanosheet dispersion (sample IT-142) obtained in Comparative Example 1, and the mixture was shaken at room temperature for 24 hours. The resultant solution was observed with a phase-contrast microscope and a fluorescence microscope. The results are shown in FIG. 11A and FIG. 11B, respectively. The crystal structures of nanosheets were able to be observed with the phase-contrast microscope. However, almost no fluorescent coloring was observed in each of the crystal structures with the fluorescence microscope, and hence it was suggested that rhodamine B was not introduced into each of the nanosheets.

Example 9. Preparation of Nanosheet, Formation of Crosslinked Body, and Introduction of Molecules 1. Formation of Uncrosslinked Nanosheet Dispersion 120 milligrams of γ-cyclodextrin was dissolved in 1 mL of ion-exchanged water, and 30 mg of α,ω-bis-hydroxy polyethylene glycol-block-polypropylene glycol-block-polyethylene glycol was added to and sufficiently dissolved in the resultant aqueous solution of γ-cyclodextrin. The solution was stirred as it was at room temperature for 1 day to provide an uncrosslinked nanosheet dispersion. The uncrosslinked nanosheet is referred to as "γ-plu108-NS".

2. Method of Producing Nanosheet Crosslinked Body

Next, 15-crown-5-ether was added to 1 mL of the γ-plu108-NS dispersion, and 19.2 mg/mL of adipic acid dichloride was further added thereto. The mixture was subjected to a reaction for 72 hours to provide a crude γ-plu108-NS crosslinked body.

3. Production of Porous Nanosheet Crosslinked Body by Removal of Axis of Nanosheet Crosslinked Body 1 Milliliter of ethanol was added to the dispersion of the crude γ-plu108-NS crosslinked body in 15-crown-5-ether, and ion-exchanged water was further added thereto. Thus, an aqueous dispersion of a porous γ-plu108-NS crosslinked body, which was a porous nanosheet crosslinked body from which a PEO-PPO-PEO chain serving as an axial molecule had been removed, was obtained.

The ratio at which the axial molecules were removed was measured by a proton nuclear magnetic resonance method. As a result, it was recognized that the number of the columns of cyclic molecules in which chain molecules (PEO-PPO-PEO) were not included accounted for about 50% of the total number of the columns of the cyclic molecules in the nanosheet.

4. Introduction of Molecules into Porous Nanosheet Crosslinked Body

A low-molecular weight compound was added, and caused to adsorb, to the aqueous dispersion of the porous γ-plu108-NS crosslinked body, and then the porous γ-plu108-NS crosslinked body was sedimented by centrifugation. The concentration of the low-molecular weight compound present in the supernatant liquid obtained at that time was determined by a UV-visible spectral method. Thus, the amount of the low-molecular weight compound adsorbing to the porous γ-plu108-NS crosslinked body was determined. The ratio of the weight of the low-molecular weight compound to the total sum of the weights of the low-molecular weight compound and the porous γ-plu108-NS crosslinked body was as follows: 0.6 wt % in the case of catechin; 0.5 wt % in the case of coumarin; and 5.3 wt % in the case of linoleic acid.

Example 10. Preparation of Microstructural Body 1, Formation of Crosslinked Body, and Introduction of Molecules 1. Formation of Uncrosslinked Microstructural Body 120 Milligrams of γ-cyclodextrin was dissolved in 1 mL of ion-exchanged water, and 30 mg of α,ω-bis-hydroxy polypropylene glycol was further added to and sufficiently dissolved in the aqueous solution of γ-cyclodextrin. The solution was stirred as it was at room temperature for 1 day to provide an uncrosslinked microstructural body dispersion. The uncrosslinked microstructural body is referred to as "γ-PPG4k-Plate".

2. Method of Producing Crosslinked Body of Microstructural Body

Next, 1 mL of the γ-PPG4k-Plate dispersion was centrifuged, and the resultant supernatant liquid was removed. After that, 15-crown-5-ether was added to the residue, and 19.2 mg/ml of adipic acid dichloride was further added thereto. The mixture was subjected to a reaction for 72 hours to provide a crude γ-PPG4k-Plate crosslinked body.

3. Crosslinked Body of Porous Microstructural Body Obtained by Removal of Axis of Crosslinked Body of Microstructural Body The dispersion of the crude γ-PPG4k-Plate crosslinked body in 15-crown-5-ether was centrifuged, and the resultant supernatant liquid was removed. After that, 1 mL of ethanol was added to the residue, and ion-exchanged water was further added thereto. Thus, an aqueous dispersion of a porous γ-PPG4k-Plate crosslinked body, which was a crosslinked body of a porous microstructural body from which a PPG chain serving as an axial molecule had been removed, was obtained.

The ratio at which the axial molecules were removed was measured by a proton nuclear magnetic resonance method. As a result, it was recognized that the number of the columns of cyclic molecules in which chain molecules (PEO-PPO-PEO) were not included accounted for about 50% of the total number of the columns of the cyclic molecules in the microstructural body.

4. Introduction of Molecules into Crosslinked Body of Porous Microstructural Body A low-molecular weight compound was added, and caused to adsorb, to the aqueous dispersion of the porous γ-PPG4k-Plate crosslinked body, and then the porous γ-PPG4k-Plate crosslinked body was sedimented by centrifugation. The concentration of the low-molecular weight compound present in the supernatant liquid obtained at that time was determined by a UV-visible spectral method. Thus, the amount of the low-molecular weight compound adsorbing to the porous γ-PPG4k-Plate crosslinked body was determined. The ratio of the weight of the low-molecular weight compound to the total sum of the weights of the low-molecular weight compound and the porous γ-PPG4k-Plate crosslinked body was as follows: 0.7 wt % in the case of catechin; 0.6 wt % in the case of coumarin; and 0.9 wt % in the case of linoleic acid. Meanwhile, biotin, rhodamine B, nicotinic acid, and dorzolamide were not introduced.

Example 11. Preparation of Microstructural Body 2, Formation of Crosslinked Body, and Purification 1. Formation of Uncrosslinked Microstructural Body 120 milligrams of γ-cyclodextrin was dissolved in 1 mL of ion-exchanged water, and 30 mg of linoleic acid was added to and sufficiently dissolved in the resultant aqueous solution of γ-cyclodextrin. The solution was stirred as it was at room temperature for 1 day to provide an uncrosslinked microstructural body dispersion. The uncrosslinked microstructural body is referred to as "γ-Lino-Plate".

2. Method of Producing Crosslinked Body of Microstructural Body

Next, 15-crown-5-ether was added to 1 mL of the γ-Lino-Plate dispersion, and 19.2 mg/ml of adipic acid dichloride was further added thereto. The mixture was subjected to a reaction for 72 hours to provide a γ-Lino-Plate crosslinked body.

3. Purification of Crosslinked Body of Microstructural Body

The dispersion of the crude γ-Lino-Plate crosslinked body in 15-crown-5-ether was centrifuged, and the resultant supernatant liquid was removed. After that, ion-exchanged water was added to the residue. Thus, an aqueous dispersion of a purified γ-Lino-Plate crosslinked body was obtained;

EXPLANATION OF REFERENCE NUMERALS

10 . . . cycle molecule, 20 . . . chain polymer serving as chain molecule, 30 . . . pseudo-polyrotaxane and/or polyrotaxane, 40, 42, 14 . . . nanosheet serving as nano or microstructural body, 40' . . . nano or microstructural body.

The invention claimed is:

1. A nano or microstructural body comprising:

a plurality of cyclic molecules each including a cavity; and a plurality of chain molecules, the plurality of chain molecules each being included in part of the plurality of cyclic molecules in a skewered manner to form a plurality of pseudo-polyrotaxanes and/or polyrotaxanes, wherein all or part of the adjacent cyclic molecules in the nano or microstructural body are crosslinked to each other, wherein the plurality of cyclic molecules arranged in series in the nano or microstructural body form a column, and the number of the columns in which the chain molecules are free from being included accounts for more than 10% of a total number of the columns in the nano or microstructural body.

2. The nano or microstructural body according to claim 1, wherein 50% or more of a total number of the cyclic molecules in the nano or microstructural body are crosslinked.

3. The nano or microstructural body according to claim 1, wherein the chain molecules in the plurality of pseudo-polyrotaxanes and/or polyrotaxanes each have, at both ends thereof or near both the ends, non-ionizable groups that are free from ionizing in water or an aqueous solution.

4. The nano or microstructural body according to claim 1, wherein the chain molecules in the plurality of pseudo-polyrotaxanes and/or polyrotaxanes each have, at both ends thereof or near both the ends, ionizable groups that ionize under conditions under which the nano or microstructural body is produced.

5. The nano or microstructural body according to claim 1, wherein the chain molecules each have, inside both ends of the chain molecule, a first region and a second region in which the cyclic molecules are absent, and the first region and the second region each have a length of from 0.5 nm to 100 nm.

6. The nano or microstructural body according to claim 1, wherein the cyclic molecules are selected from the group consisting of: α-cyclodextrin; β-cyclodextrin; γ-cyclodextrin; a crown ether; a pillararene; a calixarene; a cyclophane; a cucurbituril; and derivatives thereof.

7. The nano or microstructural body according to claim 1, wherein the cavity has included therein a substance selected from the group consisting of a drug, a fluorescent substance, and a chromogenic enzyme.

8. The nano or microstructural body according to claim 1, wherein the microstructural body is a nanosheet.

9. A substance adsorbent comprising the nano or microstructural body of claim 1.

10. A pharmaceutical comprising the nano or microstructural body of claim 1.

11. A food comprising the nano or microstructural body of claim 1.

12. A method of producing a nano or microstructural body comprising a step of crosslinking a nano or microstructural body, which includes a plurality of cyclic molecules each including a cavity and a plurality of chain molecules, and in which the plurality of chain molecules are each included in part of the plurality of cyclic molecules in a skewered manner to form a plurality of pseudo-polyrotaxanes and/or polyrotaxanes, to provide a nano or microstructural body in which all or part of the adjacent cyclic molecules are crosslinked to each other.

13. The method according to claim 12, further comprising a step of removing part or all of the plurality of chain molecules included in part of the plurality of cyclic molecules in a skewered manner.

* * * * *